(12) United States Patent
Unwalla et al.

(10) Patent No.: US 12,195,750 B2
(45) Date of Patent: *Jan. 14, 2025

(54) INDUCIBLE CRISPR SYSTEM EXPRESSION AND APPLICATIONS THEREOF

(71) Applicants: Hoshang Jehangir Unwalla, Miami, FL (US); Srinivasan Chinnapaiyan, Miami, FL (US)

(72) Inventors: Hoshang Jehangir Unwalla, Miami, FL (US); Srinivasan Chinnapaiyan, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/192,191

(22) Filed: Mar. 29, 2023

(65) Prior Publication Data
US 2023/0257780 A1    Aug. 17, 2023

Related U.S. Application Data

(63) Continuation of application No. 17/491,738, filed on Oct. 1, 2021, now Pat. No. 11,643,672.

(51) Int. Cl.
| | |
|---|---|
| *C12N 15/90* | (2006.01) |
| *C12N 9/22* | (2006.01) |
| *C12N 15/11* | (2006.01) |
| *C12N 15/85* | (2006.01) |

(52) U.S. Cl.
CPC ............. *C12N 15/907* (2013.01); *C12N 9/22* (2013.01); *C12N 15/11* (2013.01); *C12N 15/85* (2013.01); *C12N 2310/20* (2017.05); *C12N 2740/16041* (2013.01); *C12N 2830/002* (2013.01)

(58) Field of Classification Search
CPC ...... C12N 2740/16043; C12N 2310/20; C12N 2310/12–2310/123; C12N 9/22; C12N 15/11
See application file for complete search history.

(56) References Cited

U.S. PATENT DOCUMENTS

| | | |
|---|---|---|
| 8,138,327 B2 | 3/2012 | Unwalla et al. |
| 2017/0088845 A1* | 3/2017 | Ryan ..................... C12N 15/80 |
| 2020/0071671 A1 | 3/2020 | Sherer et al. |

FOREIGN PATENT DOCUMENTS

| | | | |
|---|---|---|---|
| WO | 2015099850 A1 | 7/2015 | |
| WO | WO-2016154016 A2 * | 9/2016 | ............. A61K 45/06 |
| WO | 2017106414 A1 | 6/2017 | |

OTHER PUBLICATIONS

Kim et al. Rescue of high-specificity Cas9 variants using sgRNAs with matched 5' nucleotides. Genome Biology, vol. 18, 218, Nov. 15, 2017, printed as pp. 1/6-6/6 and Additional file 1 printed as pp. 1/8-8/8. (Year: 2017).*

Hultquist et al. CRISPR-Cas9 genome engineering of primary CD4+ T cells for the interrogation of HIV-host factor interactions. Nature Protocols, vol. 14, pp. 1-27, Dec. 17, 2018. (Year: 2018).*

Ramanathan et al. mRNA capping: biological functions and applications. Nucleic Acids Research, vol. 44, No. 16, pp. 7511-7526, Jun. 17, 2016. (Year: 2016).*

GenBank Accession No. NC_000012.12, region 48716501 . . . 48716650 (publicly available Aug. 2020, printed as pp. 1/4-4/4. (Year: 2020).*

Chinnapaiyan, Srinivasan et al. "A conditional RNA Pol II monopromoter drives HIV-inducible, CRISPR-mediated cyclin T1 suppression and HIV inhibition." Molecular Therapy: Nucleic Acids 32:553-565, Jun. 2023.

Das et al. "Tet-On Systems For Doxycycline-inducible Gene Expression." Current Gene Therapy, 16(3):156-167, (Year: 2016).

Gao, Yangbin & Zhao, Yunde "Self-processing of ribozyme-flanked RNAs into guide RNAs in vitro and in vivo for CRISPR-mediated genome editing." Journal of Integrative Plant Biology, 56(4):343-349, Apr. 2014.

González, Federico et al. "An iCRISPR Platform for Rapid, Multiplexable, and Inducible Genome Editing in Human Pluripotent Stem Cells." Cell Stem Cell 15:215-226, Aug. 7, 2014.

Kaminski, Rafal et al. "Negative Feedback Regulation of HIV-1 by Gene Editing Strategy." Scientific reports 6(1):1-11, Aug. 16, 2016.

Lee et al. "Ribozyme Mediated gRNA Generation for In Vitro and In Vivo CRISPR/Cas9 Mutagenesis." PLOSone 11(11):1-12, Nov. 10, 2016.

Li, Qian et al. "In vivo PCSK9 gene editing using an all-in-one self-cleavage AAV-CRISPR system." Molecular Therapy: Methods & Clinical Development 20:652-659, Mar. 2021.

(Continued)

*Primary Examiner* — Jennifer Dunston
*Assistant Examiner* — Jenna L Persons
(74) *Attorney, Agent, or Firm* — SALIWANCHIK, LLOYD & EISENSCHENK

(57) ABSTRACT

The invention pertains to an inducible CRISPR system for controlling expression of a CRISPR complex with an inducible fusion promoter. One embodiment of the invention provides HIV LTR-minimal *Drosophila* hsp70 fusion promoter that can be used for inducible co-expression of gRNA and Cas9 in HIV-infected cells to target cellular cofactors such as Cyclin T1. A single introduction of such embodiment leads to sustained suppression of HIV replication in stringent, chronically infected HeLa-CD4 cell lines as well as in T-cell lines. In another embodiment, the invention further relates to enhancement of HIV suppression by incorporating cis-acting ribozymes immediately upstream of the gRNA in the inducible CRISPR system construct. The inducible fusion promoter is adaptable for other tissue- or cell-type specific expression of the inducible CRISPR system.

19 Claims, 8 Drawing Sheets

Specification includes a Sequence Listing.

(56) References Cited

OTHER PUBLICATIONS

O'Rourke, Sara M. & Scott, William G. "Structural Simplicity and Mechanistic Complexity in the Hammerhead Ribozyme." Progress in Molecular Biology and Translational Science 159:177-202, (Year: 2018).

Persson, Tina et al. "Selection of Hammerhead Ribozyme Variants with Low Mg2 Requirement: Importance of Stem-Loop II." ChemBioChem 3(11):1066-1071, (Year: 2002).

Petris, Gianluca et al. "Hit and go CAS9 delivered through a lentiviral based self-limiting circuit." nature communications 8(1):1-10, May 22, 2017.

St-Onge et al. "Temporal control of the Cre recombinase in transgenic mice by a tetracycline responsive promoter." Nucleic Acids Research, 24(19):3875-3877, (Year: 1996).

Unwalla, Hoshang J. et al. "Negative feedback inhibition of HIV-1 by TAT-inducible expression of siRNA." nature biotechnology 22(12):1573-1578, Nov. 28, 2004.

Unwalla, Hoshang J. et al. "Novel Pol II Fusion Promoter Directs Human Immunodeficiency Virus Type 1-Inducible Coexpression of a Short hairpin RNA and Protein." American Society for Microbiology 80(4):1863-1873, (Year: 2006).

Xia, Haibin et al. "siRNA-mediated gene silencing in vitro and in vivo." nature biotechnology 20(10):1006-1010, (Year: 2002).

Yoshioka, Shin et al. "Development of a mono-promoter-driven CRISPR/Cas9 system in mammalian cells." Scientific Reports 5(1):1-27, Dec. 16, 2015.

Zhang, Jingfang et al. "Drug Inducible CRISPR/Cas Systems." Computational and Structural Biotechnology Journal 17:1171-1177, Jul. 30, 2019.

\* cited by examiner

SEQUENCE LISTING

```
Sequence total quantity: 21
SEQ ID NO: 1           moltype = DNA  length = 28
FEATURE                Location/Qualifiers
misc_feature           1..28
                       note = 5' primer with KpnI site
source                 1..28
                       mol_type = other DNA
                       organism = synthetic construct
SEQUENCE: 1
ccggtacctg gaagggctaa tttggtcc                                    28

SEQ ID NO: 2           moltype = DNA  length = 19
FEATURE                Location/Qualifiers
misc_feature           1..19
                       note = 3' primer
source                 1..19
                       mol_type = other DNA
                       organism = synthetic construct
SEQUENCE: 2
gaggcgcttc gtctacgga                                              19

SEQ ID NO: 3           moltype = DNA  length = 23
```

```
                              -continued
FEATURE               Location/Qualifiers
misc_feature          1..23
                      note = 5' primer
source                1..23
                      mol_type = other DNA
                      organism = synthetic construct
SEQUENCE: 3
gaaacaccgt ccacgccaaa acg                                          23

SEQ ID NO: 4          moltype = DNA  length = 24
FEATURE               Location/Qualifiers
misc_feature          1..24
                      note = 3' primer
source                1..24
                      mol_type = other DNA
                      organism = synthetic construct
SEQUENCE: 4
caccgactcg gtgccacttt ttca                                         24

SEQ ID NO: 5          moltype = DNA  length = 19
FEATURE               Location/Qualifiers
misc_feature          1..19
                      note = 5' primer
source                1..19
                      mol_type = other DNA
                      organism = synthetic construct
SEQUENCE: 5
ctagaactag taataaagg                                               19

SEQ ID NO: 6          moltype = DNA  length = 25
FEATURE               Location/Qualifiers
misc_feature          1..25
                      note = 3' primer with XbaI site
source                1..25
                      mol_type = other DNA
                      organism = synthetic construct
SEQUENCE: 6
tctagatcta gacgcggccg cacac                                        25

SEQ ID NO: 7          moltype = DNA  length = 27
FEATURE               Location/Qualifiers
misc_feature          1..27
                      note = 3' primer with EcoR1 site
source                1..27
                      mol_type = other DNA
                      organism = synthetic construct
SEQUENCE: 7
ccgaattcga ggcgcttcgt ctacgga                                      27

SEQ ID NO: 8          moltype = DNA  length = 52
FEATURE               Location/Qualifiers
misc_feature          1..52
                      note = 5' primer for partial Mz
source                1..52
                      mol_type = other DNA
                      organism = synthetic construct
SEQUENCE: 8
ttcgaaacga ttttctctca aatcgtcgcg aaacaccgtc cacgccaaaa cg          52

SEQ ID NO: 9          moltype = DNA  length = 51
FEATURE               Location/Qualifiers
misc_feature          1..51
                      note = 5' primer for full ribozymes with EcoR1 site
source                1..51
                      mol_type = other DNA
                      organism = synthetic construct
SEQUENCE: 9
ccgaattctg tttcgcctga tgagttttcg aaacgatttt ctctcaaatc g           51

SEQ ID NO: 10         moltype = DNA  length = 52
FEATURE               Location/Qualifiers
misc_feature          1..52
                      note = 5' primer for partial Mzwk
source                1..52
                      mol_type = other DNA
                      organism = synthetic construct
SEQUENCE: 10
ttcgaaacga ttttctctca aatcgtggcg aaacaccgtc cacgccaaaa cg          52
```

```
SEQ ID NO: 11              moltype = DNA  length = 489
FEATURE                    Location/Qualifiers
misc_feature               1..489
                           note = HIV-1 LTR including TAR
source                     1..489
                           mol_type = other DNA
                           organism = synthetic construct
SEQUENCE: 11
tggaagggct aatttggtcc caaaaaagac aagagatcct tgatctgtgg atctaccaca   60
cacaaggcta cttccctgat tggcagaact acacaccagg gccagggatc agatatccac  120
tgacctttgg atggtgcttc aagttagtac cagttgaacc agagcaagta gaagaggcca  180
atgaaggaga gaacaacagc ttgttacacc ctatgagcca gcatgggatg gaggacccgg  240
agggagaagt attagtgtgg aagtttgaca gcctcctagc atttcgtcac atggcccgag  300
agctgcatcc ggagtactac aaagactgct gacatcgagc tttctacaag ggactttccg  360
ctggggactt tccagggagg tgtggcctgg gcgggactgg ggagtggcga gccctcagat  420
gctacatata agcagctgct ttttgcctgt actgggtctc tctggttaga ccagatctga  480
gcctgggag                                                          489

SEQ ID NO: 12              moltype = DNA  length = 45
FEATURE                    Location/Qualifiers
misc_feature               1..45
                           note = Minimal Drosophila hsp70 promoter
source                     1..45
                           mol_type = other DNA
                           organism = synthetic construct
SEQUENCE: 12
taccctcgac cgccggagta taaatagagg cgcttcgtct acgga                  45

SEQ ID NO: 13              moltype = DNA  length = 20
FEATURE                    Location/Qualifiers
misc_feature               1..20
                           note = Cyclin T1 gRNA-1 guide
source                     1..20
                           mol_type = other DNA
                           organism = synthetic construct
SEQUENCE: 13
aatagcccat cccgtcgttt                                              20

SEQ ID NO: 14              moltype = DNA  length = 20
FEATURE                    Location/Qualifiers
misc_feature               1..20
                           note = Cyclin T1 gRNA-2 guide
source                     1..20
                           mol_type = other DNA
                           organism = synthetic construct
SEQUENCE: 14
tccacgccaa aacgacggga                                              20

SEQ ID NO: 15              moltype = DNA  length = 20
FEATURE                    Location/Qualifiers
misc_feature               1..20
                           note = Cyclin T1 gRNA-3 guide
source                     1..20
                           mol_type = other DNA
                           organism = synthetic construct
SEQUENCE: 15
cctacctcac ttctagtatc                                              20

SEQ ID NO: 16              moltype = DNA  length = 53
FEATURE                    Location/Qualifiers
misc_feature               1..53
                           note = Mz ribozyme
source                     1..53
                           mol_type = other DNA
                           organism = synthetic construct
SEQUENCE: 16
tgtttcgcct gatgagtttt cgaaacgatt ttctctcaaa tcgtcgcgaa aca          53

SEQ ID NO: 17              moltype = DNA  length = 53
FEATURE                    Location/Qualifiers
misc_feature               1..53
                           note = Mzwk ribozyme
source                     1..53
                           mol_type = other DNA
                           organism = synthetic construct
SEQUENCE: 17
tgtttcgcct gatgagtttt cgaaacgatt ttctctcaaa tcgtggcgaa aca          53

SEQ ID NO: 18              moltype = DNA  length = 13095
```

| FEATURE | Location/Qualifiers |
|---|---|
| misc_feature | 1..13095 |
| | note = LTRhsp-gRNA-mpolyA-Cas9pA |
| source | 1..13095 |
| | mol_type = other DNA |
| | organism = synthetic construct |

SEQUENCE: 18

```
gtcgacggat cgggagatct cccgatcccc tatggtgcac tctcagtaca atctgctctg   60
atgccgcata gttaagccag tatctgctcc ctgcttgtgt gttggaggtc gctgagtagt  120
gcgcgagcaa aatttaagct acaacaaggc aaggcttgac cgacaattgc atgaagaatc  180
tgcttagggt taggcgtttt gcgctgcttc gcgatgtacg ggccagatat acgcgttgac  240
attgattatt gactagttat taatagtaat caattacggg gtcattagtt catagcccat  300
atatggagtt ccgcgttaca taacttacgg taaatggccc gcctggctga ccgcccaacg  360
acccccgccc attgacgtca ataatgacgt atgttcccat agtaacgcca atagggactt  420
tccattgacg tcaatgggtg gagtatttac ggtaaactgc ccacttggca gtacatcaag  480
tgtatcatat gccaagtacg ccccctattg acgtcaatga cggtaaatgg cccgcctggc  540
attatgccca gtacatgacc ttatgggact ttcctacttg gcagtacatc tacgtattag  600
tcatcgctat taccatggtg atgcggtttt ggcagtacat caatgggcgt ggatagcggt  660
ttgactcacg gggatttcca agtctccacc ccattgacgt caatgggagt ttgttttggc  720
accaaaatca acgggacttt ccaaaatgtc gtaacaactc cgccccattg acgcaaatgg  780
gcggtaggcg tgtacggtgg gaggtctata taagcagcgc gttttgcctg tactgggtct  840
ctctggttag accagatctg agcctgggag ctctctggct aactagggaa cccactgctt  900
aagcctcaat aaagcttgcc ttgagtgctt caagtagtgt gtgcccgtct gttgtgtgac  960
tctggtaact agagatccct cagacccttt tagtcagtgt ggaaaatctc tagcagtggc 1020
gcccgaacag ggacttgaaa gcgaaaggga accagagga gctctctcga cgcaggactc 1080
ggcttgctga agcgcgcacg gcaagaggcg agggggcgcg actggtgagt acgccaaaaa 1140
ttttgactag cggaggctag aaggagagag atgggtgcga gagcgtcagt attaagcggg 1200
ggagaattag atcgcgatgg gaaaaaattc ggttaaggcc agggggaaag aaaaaatata 1260
aattaaaaca tatagtatgg gcaagcaggg agctagaacg attcgcagtt aatcctggcc 1320
tgttagaaac atcagaaggc tgtagacaaa tactgggaca gctacaacca tcccttcaga 1380
caggatcaga agaacttaga tcattatata atacagtagc aaccctctat tgtgtgcatc 1440
aaaggataga gataaaagac accaaggaag ctttagacaa gatagaggaa gagcaaaaca 1500
aaagtaagac caccgcacag caagcggccg ctgatcttca gacctggagg aggagatatg 1560
agggacaatt ggagaagtga attatataaa tataaagtag taaaaattga accattagga 1620
gtagcaccca ccaaggcaaa gagaagagtg gtgcagagag aaaaaagagc agtgggaata 1680
ggagctttgt tccttgggtt cttgggagca gcaggaagca ctatgggcgc agcgtcaatg 1740
acgctgacgg tacaggccag acaattattg tctggtatag tgcagcagca gaacaatttg 1800
ctgagggcta ttgaggcgca acagcatctg ttgcaactca cagtctgggg catcaagcag 1860
ctccagcaa gaatcctggc tgtggaaaga tacctaaagg atcaacagct cctggggatt 1920
tggggttgct ctggaaaact catttgcacc actgctgtgc cttggaatgc tagttggagt 1980
aataaatctc tggaacagat ttggaatcac acgacctgga tggagtggga cagagaaatt 2040
aacaattaca caagcttaat acactcctta attgaagaat cgcaaaacca gcaagaaaag 2100
aatgaacaag aattattgga attagataaa tgggcaagtt tgtggaattg gtttaacata 2160
acaaattggc tgtggtatat aaaattattc ataatgatag taggaggctt ggtaggttta 2220
agaatagttt ttgctgtact ttctatagtg aatagagtta ggcagggata ttcaccatta 2280
tcgtttcaga cccacctccc aacccgagg ggaccccgaca ggcccgaagg aatagaagaa 2340
gaaggtggag agagacagag acagatcc attcgattag tgaacggatc ggcactgcgt 2400
gcgccaattc tgcagacaaa tggcagtatt catccacaat tttaaaagaa aaggggggat 2460
tgggggggtac agtgcagggg aaagaatagt agacataata gcaacagaca tacaaactaa 2520
agaattacaa aaacaaatta caaaaattca aaattttcgg gtttattaca gggacagcag 2580
agatccagtt tggttaatta aggtacctgg aagggctaat ttggtcccaa aaaagacaag 2640
agatccttga tctgtggatc taccacacac aaggctactt ccctgattgg cagaactaca 2700
caccagggcc agggatcaga tatccactga cctttggatg gtgcttcaag ttagtaccag 2760
ttgaaccaga gcaagtagaa gaggccaatg aaggagagaa caacagcttg ttacacccta 2820
tgagccagca tgggatggag gacccggagg gagaagtatt agtgtggaag tttgacagcc 2880
tcctagcatt tcgtcacatg gcccgagagc tgcatccgga gtactacaaa gactgctgac 2940
atcgagcttt ctacaaggga ctttccgctg gggactttcc agggaggtgt ggcctgggcg 3000
ggactgggga gtggcgagcc ctcagatgct acatataagc agctgctttt tgcctgtact 3060
gggtctctct ggttagacca gatctgagcc tgggagtacc ctcgaccgcc ggagtataaa 3120
tagaggcgct tcgtctacgg agaaacaccg tccacgccaa aacgacggga gtttagagc 3180
tagaaatagc aagttaaaat aaggctagtc cgttatcaac ttgaaaaagt ggcaccgagt 3240
cggtgcctag aactagtaat aaaggatcct tattttcat tggatccgtg tgttggtttt 3300
ttgtgtgcgc ccgcgtctag agcgctgcca ccatggacaa gaagtacagc atcggcctgg 3360
acatcggcac caactctgtg ggctgggccg tgatcacgga cgagtacaag gtgccctcca 3420
agaaattcaa ggtgctgggc aacaccgacc ggcacagcat caagaagaac ctgatcggag 3480
ccctgctgtt cgacagcggc gaaacagccg aggccaccc gctgaagaga accgccagaa 3540
gaagatacac cagacggaag aaccggatct gctatctgca agagatcttc agcaacgaga 3600
tggccaaggt ggacgacagc ttcttccaca gactggaaga gtccttcctg gtggaagagg 3660
ataagaagca cgagcggcac cccatcttcg gcaacatcgt ggacgaggtg gcctaccacg 3720
agaagtaccc caccatctac cacctgagaa agaaactggt ggacagcacc gacaaggccg 3780
acctgcggct gatctatctg gccctggccc acatgatcaa gttccggggc cacttcctga 3840
tcgagggcga cctgaacccc gacaacagcg acgtggacaa gctgttcatc cagctggtgc 3900
agacctacaa ccagctgttc gagaaaaacc ccatcaacgc cagcggcgtg gacgccaagg 3960
ccatcctgtc tgccagactg agcaagagca gacggctgga aaatctgatc gcccagctgc 4020
ccggcgagaa gaagaatggc ctgttcggaa acctgattgc cctgagcctg ggcctgaccc 4080
ccaacttcaa gagcaacttc gacctggccg aggatgccaa actgcagctg agcaaggaca 4140
cctacgacga cgacctggac aacctgctgg cccagatcgg cgaccagtac gccgacctgt 4200
ttctggccgc caagaacctg tccgacgcca tcctgctgag cgacatcctg agagtgaaca 4260
ccgagatcac caaggccccc ctgagcgcct ctatgatcaa gagatacgac gagcaccacc 4320
```

```
aggacctgac cctgctgaaa gctctcgtgc ggcagcagct gcctgagaag tacaaagaga 4380
ttttcttcga ccagagcaag aacggctacg ccggctacat tgacggcgga gccagccagg 4440
aagagttcta caagttcatc aagcccatcc tggaaaagat ggacggcacc gaggaactgc 4500
tcgtgaagct gaacagagag gacctgctgc ggaagcagcg gaccttcgac aacggcagca 4560
tcccccacca gatccacctg ggagagctgc acgccattct gcggcggcag gaagattttt 4620
acccattcct gaaggacaac cggaaaaaga tcgagaagat cctgaccttc cgcatcccct 4680
actacgtggg ccctctggcc aggggaaaca gcagattcgc ctggatgacc agaaagagcg 4740
aggaaaccat cacccctgg aacttcgagg aagtggtgga caaggcgct tccgcccaga 4800
gcttcatcga gcggatgacc aacttcgata agaacctgcc caacgagaag gtgctgccca 4860
agcacagcct gctgtacgag tacttcaccg tgtataacga gctgaccaaa gtgaaatacg 4920
tgaccgaggg aatgagaaag cccgccttcc tgagcggcga gcagaaaaag gccatcgtgg 4980
acctgctgtt caagaccaac cggaaagtga ccgtgaagca gctgaagag gactacttca 5040
agaaaatcga gtgcttcgac tccgtggaaa tctccggcgt ggaagatcgg ttcaacgcct 5100
ccctgggcac ataccacgat ctgctgaaaa ttatcaagga caaggacttc ctggacaatg 5160
aggaaaacga ggacattctg gaagatatcg tgctgaccct gacactgttt gaggacagag 5220
agatgatcga ggaacggctg aaaacctatg cccaccgtt cgacgacaaa gtgatgaagc 5280
agctgaagcg gcggagatac accggctggg gcaggctgag ccggaagctg atcaacggca 5340
tccgggacaa gcagtccggc aagacaatcc tggatttcct gaagtccgac ggcttcgcca 5400
acagaaactt catgcagctg atccacgacg acagcctgac cttta aagag gacatccaga 5460
aagcccaggt gtccggccag ggcgatagcc tgcacgagca cattgccaat ctggccggca 5520
gccccgccat taagaagggc atcctgcaga cagtgaaggt ggtggacgag ctcgtgaaag 5580
tgatggccg gcacaagccc gagaacatcg tgatcgaaat ggcagagag aaccagacca 5640
cccagaaggg acagaagaac agccgcgaga gaatgaagcg gatcgaagag ggcatcaaag 5700
agctgggcag ccagatcctg aaagaacacc ccgtggaaaa cacccagctg cagaacgaga 5760
agctgtacct gtactacctg cagaatgggc gggatatgta cgtggaccag gaactggaca 5820
tcaacgagct gtccgactac gatgtggacc atatcgtgcc tcagagcttt ctgaaggacg 5880
actccatcga caacaaggtg ctgaccagaa gcgacaagaa ccggggcaag agcgacaacg 5940
tgccctccga agaggtcgtg aagaagatga agaactactg gcggcagctg ctgaacgcca 6000
agctgattac ccagagaaag ttcgacaatc tgaccaaggc cgagagaggc ggcctgagcg 6060
aactggataa ggccggcttc atcaagagac agctggtgga aacccgccaa gatcacaaagc 6120
acgtggcaca gatcctggac tcccggatga acactaagta cgacgagaat gacaagctga 6180
tccgggaagt gaaagtgatc accctgaagt ccaagctggt gtccgatttc cggaaggatt 6240
tccagtttta caaagtgcgc gagatcaaca actaccacca cgcccacgac gcctacctga 6300
acgccgtcgt gggaaccgcc ctgatcaaaa agtaccctaa gctggaaagc gagttcgtgt 6360
acggcgacta caaggtgtac gacgtgcgga agatgatcgc caagagcgag caggaaatcg 6420
gcaaggctac cgccaagtac ttcttctaca gcaacatcat gaacttttc aagaccgaga 6480
ttaccctggc caacgcgag atccggaagc ggcctctgat cgagacaaac ggcgaaaccg 6540
gggagatcgt gtgggataag ggccgggatt ttgccaccgt gcggaaagtg ctgagcatgc 6600
cccaagtgaa tatcgtgaaa aagaccgagg tgcagacagg cggcttcagc aaagagtcta 6660
tcctgcccaa gaggaacagc gataagctga tcgccagaaa aaggactgg gaccctaaga 6720
agtacggcgg cttcgacagc cccaccgtgg cctattctgt gctggtggtg gccaaagtgg 6780
aaaagggcaa gtccaagaaa ctgaagagtg tgaaagagct gctgggatc accatcatgg 6840
aaagaagcag cttcgagaag aatccatcg actttctgga agccaaggc tacaaagaag 6900
tgaaaaagga cctgatcatc aagctgccta gtactccct gttcgagctg gaaaacggcc 6960
ggaagagaat gctggcctct gccggcgaac tgcagaaggg aaacgaactg gccctgcct 7020
ccaaatatgt gaacttcctg tacctggcca gccactatga gaagctgaag ggctcccccg 7080
aggataatga gcagaaacag ctgtttgtgg aacagcacaa gcactacctg gacgagatca 7140
tcgagcagat cagcgagttc tccaagagag tgatcctggc cgacgctaat ctggacaaag 7200
tgctgtccgc ctacaacaag caccgggata agcccatcag agagcaggcc gagaatatca 7260
tccacctgtt taccctgacc aatctgggag ccctgccgc cttcaagtac tttgacacca 7320
ccatcgaccg gaagaggtac accagcacca aagaggtgct ggacgccacc ctgatccaca 7380
agagcatcac cggcctgtac gagacacgga tcgacctgtc tcagctggga ggcgacaagc 7440
gacctgccgc cacaaagaag gctggacagg ctaagaagaa gaaagattac aaagacgatg 7500
acgataaggg atccggcgca acaaacttct ctctgctgaa acaagccgga gatgtcgaag 7560
agaatcctgg accgaccgag tacaagccca cggtgcgcct cgccaccgc gacgacgtcc 7620
ccagggccgt acgcacctc gccgccgcgt tcgccgacta ccccgccacg gcgccacccg 7680
tcgatccgga ccgccacatc gagcgggtca ccgagctgca agaactcttc ctcacgcgcg 7740
tcgggctcga tcggcaag gtgtgggcg cggacgacgg cgccgcggtg gcggtctgga 7800
ccacgccgga gagcgtcgaa gcggggcgg tgttcgccga gatcggcccg cgcatggccg 7860
agttgagcgg ccggctg gccgcgcagc aacagatgga aggcctcctg gcgccgcacc 7920
ggcccaagga gcccgcgtgg ttcctggcca ccgtcggagt ctcgcccgac caccagggca 7980
agggtctggg cagcgcgtc gtgctccccg gagtggaggc ggccgagcgc gccggggtgc 8040
ccgccttcct ggagacctcc gcgccccgca acctcccctt ctacgagcgg ctcggcttca 8100
ccgtcaccgc cgacgtcgag gtgcccgaag accgcctgctgcatg acccgcaagc 8160
ccggtgcctg aacgcgttaa gtcgacaatc aacctctgga ttacaaaatt tgtgaaagat 8220
tgactggtat tcttaactat gttgctcctt ttacgctatg tggatacgct gctttaatgc 8280
ctttgtatca tgctattgct tcccgtatgg ctttcatttt ctcctccttg tataaatcct 8340
ggttgctgtc tctttatgag gagttgtggc ccgttgtcag gcaacgtggc gtggtgtgca 8400
ctgtgtttgc tgacgcaacc cccactggtt ggggcattgc caccacctgt cagctccttt 8460
ccgggacttt cgcttccc ctccctattg ccacggcgga actcatcgcc gcctgccttg 8520
cccgctgctg gacaggggct cggctgttgg gcactgacaa ttccgtggtg ttgtcgggga 8580
aatcatcgtc cttccttgg ctgctcgcct gtgttgccac ctggattctg cgcgggacgt 8640
ccttctgcta cgtcccttcg ccctcaatc cagcggacct tccttcccgc ggcctgctgc 8700
cggctctgcg gcctcttccg cgtcttcgcc ttcgccctca gacgagtcgg atctccctt 8760
gggccgcctc cccgcgtcga ctttaagacc aatgacttac aaggcagctg tagatcttag 8820
ccactttttta aaagaaaagg gggactgga agggctaatt cactcccaac gaagacaaga 8880
tctgctttttt gcttgtactg ggtctctctg gttagaccag atctgagcct gggagctctc 8940
tggctaacta gggaacccac tgcttaagcc tcaataaagc ttgccttgag tgcttcaagt 9000
agtgtgtgcc cgtctgttgt gtgactctgg taactagaga tccctcagac ccttttagtc 9060
```

```
agtgtggaaa atctctagca gggcccgttt aaacccgctg atcagcctcg actgtgcctt    9120
ctagttgcca gccatctgtt gtttgcccct ccccgtgcc ttccttgacc ctggaaggtg    9180
ccactcccac tgtcctttcc taataaaatg aggaaattgc atcgcattgt ctgagtaggt    9240
gtcattctat tctgggggt ggggtggggc aggacagcaa gggggaggat tgggaagaca    9300
atagcaggca tgctgggat gcggtgggct ctatggcttc tgaggcggaa agaaccagct    9360
ggggctctag ggggtatccc cacgcgcccc gtagcggcgc attaagcgcg gcgggtgtgg    9420
tggttacgcg cagcgtgacc gctacacttg ccagcgccct agcgcccgct cctttcgctt    9480
tcttcccttc ctttctcgcc acgttcgccg gctttccccg tcaagctcta atcgggggc    9540
tcccttagg gttccgattt agtgctttac ggcacctcga ccccaaaaaa cttgattagg    9600
gtgatggttc acgtagtggg ccatcgcct gatagacggt ttttcgccct ttgacgttgg    9660
agtccacgtt ctttaatagt ggactcttgt tccaaactgg aacaacactc aaccctatct    9720
cggtctattc ttttgattta taagggattt tgccgatttc ggcctattgg ttaaaaaatg    9780
agctgattta acaaaaattt aacgcgaatt aattctgtgg aatgtgtgtc agttagggtg    9840
tggaaagtcc ccaggctccc cagcaggcag aagtatgcaa agcatgcatc tcaattagtc    9900
agcaaccagg tgtggaaagt ccccaggctc cccagcaggc agaagtatgc aaagcatgca    9960
tctcaattag tcagcaacca tagtcccgcc cctaactccg cccatcccgc cctaactcc   10020
gcccagttcc gcccattctc cgccccatgg ctgactaatt ttttttattt atgcagaggc   10080
cgaggccgcc tctgcctctg agctattcca gaagtagtga ggaggctttt ttggaggcct   10140
aggcttttgc aaaaagctcc cgggagcttg tatatccatt ttcggatctg atcagcacgt   10200
gttgacaatt aatcatcggc atagtatatc ggcatagtat aatacgacaa ggtgaggaac   10260
taaaccatgg ccaagttgac cagtgccgtt ccggtgctca ccgcgcgcga cgtcgccgga   10320
gcggtcgagt tctggaccga ccggctcggg ttctcccggg acttcgtgga cgacttc   10380
gccggtgtgg tccgggacga cgtgaccctg ttcatcagcg cggtccagga ccaggtggtg   10440
ccggacaaca ccctggcctg ggtgtgggtg cgcggcctgg acgagctgta cgccgagtgg   10500
tcggaggtcg tgtccacgaa cttccgggac gcctccgggc cggccatgac cgagatcggc   10560
gagcagccgt gggggcggga gttcgccctg cgcgaccggg ccggcaactg cgtgcacttc   10620
gtggccgagg agcaggactg acacgtgcta cgagatttcg attccaccgc cgccttctat   10680
gaaaggttgg gcttcggaat cgttttccgg gacgccggct ggatgatcct ccagcgcggg   10740
gatctcatgc tggagttctt cgcccacccc aacttgttta ttgcagctta taatggttac   10800
aaataaagca atagcatcac aaatttcaca aaataaagca tttttttcact gcattctagt   10860
tgtggtttgt ccaaactcat caatgtatct tatcatgtct gtataccgtc gacctctagc   10920
tagagcttgg cgtaatcatg gtcatagctg tttcctgtgt gaaattgtta tccgctcaca   10980
attccacaca acatacgagc cggaagcata agtgtaaagc ctggggtgc ctaatgagtg   11040
agctaactca cattaattgc gttgcgctca ctgcccgctt tccagtcggg aaacctgtcg   11100
tgccagctgc attaatgaat cggccaacgc gcggggagag gcggtttgcg tattgggcgc   11160
tcttccgctt cctcgctcac tgactcgctg cgctcggtcg ttcggctgcg gcgagcggta   11220
tcagctcact caaaggcggt aatacggtta tccacagaat caggggataa cgcaggaaag   11280
aacatgtgag caaaaggcca gcaaaaggcc aggaaccgta aaaaggccgc gttgctggcg   11340
ttttccata ggctccgccc cctgacgag catcacaaaa atcgacgctc aagtcagagg   11400
tggcgaaacc cgacaggact ataaagatac caggcgtttc ccctggaag ctccctcgtg   11460
cgctctcctg ttccgaccct gccgcttacc ggatacctgt ccgcctttct cccttcggga   11520
agcgtggcgc tttctcatag ctcacgctgt aggtatctca gttcggtgta ggtcgttcgc   11580
tccaagctgg gctgtgtgca cgaaccccc gttcagcccg accgctgcgc cttatccggt   11640
aactatcgtc ttgagtccaa cccggtaaga cacgacttat cgccactggc agcagccact   11700
ggtaacagga ttagcagagc gaggtatgta ggcggtgcta cagagttctt gaagtggtgg   11760
cctaactacg gctacactag aagaacagta tttggtatct gcgctctgct gaagccagtt   11820
accttcggaa aaagagttgg tagctcttga tccggcaaac aaaccaccgc tggtagcggt   11880
ggtttttttg tttgcaagca gcagattacg cgcagaaaaa aaggatctca agaagatcct   11940
ttgatcttt ctacggggtc tgacgctcag tggaacgaaa actcacgtta agggattttg   12000
gtcatgagat tatcaaaaag gatcttcacc tagatccttt taaattaaaa atgaagtttt   12060
aaatcaatct aaagtatata tgagtaaact tggtctgaca gttaccaatg cttaatcagt   12120
gaggcaccta tctcagcgat ctgtctattt cgttcatcca tagttgcctg actccccgtc   12180
gtgtagataa ctacgatacg ggagggctta ccatctggcc ccagtgctgc aatgataccg   12240
cgagacccac gctcaccggc tccagattta tcagcaataa accagccagc cggaagggcc   12300
gagcgcagaa gtggtcctgc aactttatcc gcctccatcc agtctattaa ttgttgccgg   12360
gaagctagag taagtagttc gccagttaat agtttgcgca acgttgttgc cattgctaca   12420
ggcatcgtgg tgtcacgctc gtcgtttggt atggcttcat tcagctccgg ttcccaacga   12480
tcaaggcgag ttacatgatc ccccatgttg tgcaaaaaag cggttagctc cttcggtcct   12540
ccgatcgttg tcagaagtaa gttggccgca gtgttatcac tcatggttat ggcagcactg   12600
cataattctc ttactgtcat gccatccgta agatgctttt ctgtgactgg tgagtactca   12660
accaagtcat tctgagaata gtgtatgcgg cgaccgagtt gctcttgccc ggcgtcaata   12720
cgggataata ccgcgccaca tagcagaact ttaaaagtgc tcatcattgg aaaacgttct   12780
tcggggcgaa aactctcaag gatcttaccg ctgttgagat ccagttcgat gtaacccact   12840
cgtgcaccca actgatcttc agcatctttt actttcacca gcgtttctgg gtgagcaaaa   12900
acaggaaggc aaaatgccgc aaaaaaggga ataagggcga cacggaaatg ttgaatactc   12960
atactcttcc tttttcaata ttattgaagc atttatcagg gttattgtct catgagcgga   13020
tacatatttg aatgtattta gaaaaataaa caaatagggg ttccgcgcac atttccccga   13080
aaagtgccac ctgac                                                    13095

SEQ ID NO: 19         moltype = DNA   length = 13148
FEATURE               Location/Qualifiers
misc_feature          1..13148
                      note = LTRhsp-MzgRNA-mpolyA-Cas9pA
source                1..13148
                      mol_type = other DNA
                      organism = synthetic construct
SEQUENCE: 19
gtcgacggat cgggagatct cccgatcccc tatggtgcac tctcagtaca atctgctctg     60
atgccgcata gttaagccag tatctgctcc ctgcttgtgt gttggaggtc gctgagtagt    120
```

```
gcgcgagcaa aatttaagct acaacaaggc aaggcttgac cgacaattgc atgaagaatc    180
tgcttagggt taggcgtttt cgcctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360
accccgccc attgacgtca ataatgacgt atgttccat agtaacgcca atagggactt    420
tccattgacg tcaatgggtg gagtattac ggtaaactgc ccacttggca gtacatcaag    480
tgtatcatat gccaagtacg cccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtcctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa   1140
ttttgactag cggaggctaa aaggagagag atggggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagaa aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aacccgagg ggacccgaca ggcccgaagg aatagaagaa   2340
gaaggtggag agagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta aggtacctgg aagggctaat ttggtcccaa aaaagacaag   2640
agatccttga tctgtggatc taccacacac aaggctactt ccctgattgg cagaactaca   2700
caccagggcc agggatcaga tatccactga cctttggatg gtgcttcaag ttagtaccag   2760
ttgaaccaga gcaagtagaa gaggccaatg aaggagagaa caacagcttg ttacacccta   2820
tgagccagca tgggatggag gacccggagg gagaagtatt agtgtggaag tttgacagcc   2880
tcctagcatt tcgtcacatg gcccgagagc tgcatccgga gtactacaaa gactgctgac   2940
atcgagcttt ctacaaggga ctttccgctg ggactttcc agggaggtgt ggcctgggcg   3000
ggactgggga gtggcgagcc ctcagatgct acatataagc agctgctttt tgcctgtact   3060
gggtctctct ggttagacca gatctgagcc tgggagtacc ctcgaccgcc ggagtataaa   3120
tagaggcgct tcgtctacgg agaattctgt ttcgcctgat gagttttcga aacgattttc   3180
tctcaaatcg tcgcgaaaca ccgtccacgc caaaacgacg ggagttttag agctagaaat   3240
agcaagttaa aataaggcta gtccgttatc aacttgaaaa agtggcaccg agtcggtgcc   3300
tagaactagt aataaaggat cctttatttt cattggatcc gtgtgttggt ttttttgtgtg   3360
cggccgcgtc tagagcgctg ccaccatgga caagaagtac agcatcggcc tggacatcgg   3420
caccaactct gtgggctggg ccgtgatcac cgacgagtac aaggtgccca gcaagaaatt   3480
caaggtgctg ggcaacaccg accggcacag catcaagaag aacctgatcg gagccctgct   3540
gttcgacagc ggcgaaacag ccgaggccac ccggctgaag agaaccgcca gaagaagata   3600
caccagacga aagaaccgga tctgctatct gcaagagatc ttcagcaacg agatggccaa   3660
ggtggacgac agcttcttcc acagactgga agagtcccttc ctggtggaag aggataagaa   3720
gcacgagcgg caccccatct cggcaacat cgtggacgag gtggcctacc acgagaagta   3780
ccccaccatc taccacctga gaaagaaact ggtggacagc accgacaagg ccgacctgcg   3840
gctgatctat ctggccctgg cccacatgat caagttccgg ggccacttcc tgatcgaggg   3900
cgacctgaac cccgacaaca gcgacgtgga caagctgttc atccagctgg tgcagaccta   3960
caaccagctg ttcgaggaaa acccatcaa cgccagcggc gtggacgcca aggccatcct   4020
gtctgccaga ctgagcaaga gcagacgact ggaaaatctg atcgcccagc tgcccggcga   4080
gaagaagaat ggcctgttcg gcaaacctga tgccctgagc ctgggcctga ccccaacctt   4140
caagagcaac ttcgacctgg ccgaggatgc caaactgcag ctgagcaagg acacctacga   4200
cgacgacctg gacaacctgc tggcccagat cggcgaccag tacgccgacc tgtttctgga   4260
cgccaagaac ctgtccgacg ccatcctgct gagcgacatc ctgagagtga acaccgagat   4320
caccaaggcc cccctgagcg cctctatgat caagagatac gacgagcacc accaggacct   4380
gaccctgctg aaagctctcg tgcggcagca gctgcctgag aagtacaaag attttctt   4440
cgaccagagc aagaacggct acgccggcta cattgacggc ggagcagcc aggaagagtt   4500
ctacaaattc atcaagccca tcctggaaaa gatggacgga accgaggaca tgctcgtgaa   4560
gctgaacaga gaggacctgc tgcggaagca gcgcaccttc gacaacggca gcatccccca   4620
ccagatccac ctgggagagc tgcacgccat tctgcggcgg caggaagatt tttacccatt   4680
cctgaaggac aaccgggaaa agatcgagaa gatcctgacc ttccgcatcc cctactacgt   4740
gggccctctc gccaggggaa acagcagatt cgcctggatg accagaaaga gcgaggaaac   4800
catcacccc tggaacttcg aggaagtggt ggacaagggc gcttccgccc agagcttcat   4860
```

```
cgagcggatg accaacttcg ataagaacct gcccaacgag aaggtgctgc ccaagcacag   4920
cctgctgtac gagtacttca ccgtgtataa cgagctgacc aaagtgaaat acgtgaccga   4980
gggaatgaga aagcccgcct tcctgagcgg cgagcagaaa aaggccatcg tggacctgct   5040
gttcaagacc aaccggaaag tgaccgtgaa gcagctgaaa gaggactact tcaagaaaat   5100
cgagtgcttc gactccgtgg aaatctccgg cgtggaagat cggttcaacg cctccctggg   5160
cacataccac gatctgctga aaattatcaa ggacaaggac ttcctggaca atgaggaaaa   5220
cgaggacatt ctggaagata tcgtgctgac cctgacactg tttgaggaca gagagatgat   5280
cgaggaacgg ctgaaaacct atgcccacct gttcgacgac aaagtgatga agcagctgaa   5340
gcggcggaga tacaccggct ggggcaggct gagccggaag ctgatcaacg gcatcccgga   5400
caagcagtcc ggcaagacaa tcctggattt cctgaagtcc gacggcttcg ccaacagaaa   5460
cttcatgcag ctgatccacg acgacagcct gaccttTaaa gaggacatcc agaaagccca   5520
ggtgtccggc cagggcgata gcctgcacga gcacattgcc aatctggccg gcagccccgc   5580
cattaagaag ggcatcctgc agacagtgaa ggtggtggac gagctcgtga aagtgatggg   5640
ccggcacaag cccgagaaca tcgtgatcga aatggccaga gagaaccaga ccacccagaa   5700
gggacagaag aacagccgcg agagaatgaa gcggatccga gagggcatca aagagctggg   5760
cagccagatc ctgaaagaac accccgtgga aaacacccag ctgcagaacg agaagctgta   5820
cctgtactac ctgcagaatg gcggggatat gtacgtggac caggaactgg acatcaaccg   5880
gctgtccgac tacgatgtgg accatatcgt gcctcagagc ttcctgaagg acgactccat   5940
cgacaacaag gtgctgacca gaagcgacaa gaaccggggc aagagcgaca acgtgccctc   6000
cgaagaggtc gtgaagaaga tgaagaacta ctggcggcag ctgctgaacg ccaagctgat   6060
tacccagaga aagttcgaca atctgaccaa ggccgagaga ggcggcctga gcgaactgga   6120
taaggccggc ttcatcaaga cagctggt ggaaaccggg cagatcacaa agcacgtggc   6180
acagatcctg gactcccgga tgaacactaa gtacgacgag aatgacaagc tgatcccgga   6240
agtgaaagtg atcaccctga agtccaagct ggtgtccgat ttccggaagg atttccagtt   6300
ttacaaagtg cgcgagatca caactacca ccacgcccac gacgcctacc tgaacgccgt   6360
cgtgggaacc gccctgatca aaaagtaccc taagctggaa agcgagttcg tgtacggcga   6420
ctacaaggtg tacgacgtgc ggaagatgat cgccaagagc gagcaggaaa tcggcaaggc   6480
taccgccaag tacttcttct acagcaacat catgaacttt ttcaagaccg agattaccct   6540
ggccaacggc gagatccgga agcggcctct gatcgagaca aacggcgaaa ccgggggagat   6600
cgtgtgggat aagggccggg attttgccac cgtgcggaaa gtgctgagca tgccccaagt   6660
gaatatcgtg aaaaagaccg aggtgcagac aggcggcttc agcaaagagt ctatcctgcc   6720
caagaggaac agcgataagc tgatcgcag aaagaaggac tgggacccta gaagtacgg   6780
cggcttcgac agccccaccg tggcctattc tgtgctggtg gtggccaaag tggaaaaggg   6840
caagtccaag aaactgaaga gtgtgaaaga gctgctgggg atcaccatca tggaaagaag   6900
cagcttcgag aagaatccca tcgactttct ggaagccaag ggctacaaag aagtgaaaaa   6960
ggacctgatc atcaagctgc ctaagtactc cctgttcgag ctggaaaacg gccgaagag   7020
aatgctggcc tctgccggcg aactgcagaa gggaaacgaa ctggccctgc cctccaaata   7080
tgtgaacttc ctgtacctgg ccagccacta tgagaagctg aagggctccc ccgaggataa   7140
tgagcagaaa cagctgtttg tggaacagca caagcactac ctggacgaga tcatcgagca   7200
gatcagcgag ttctccaaga gagtgatcct ggccgacgct aatctggaca aagtgctgtc   7260
cgcctacaac aagcaccggg ataagcccat cagagagcag gccgagaata tcatccacct   7320
gtttaccctg accaatctgg gagcccctgc cgccttcaag tactttgaca ccaccatcga   7380
ccggaaggg tacaccagca ccaaagaggt gctggacagc accctgatcc accagagcat   7440
caccggcctg tacgagacac ggatcgacct gtctcagctg ggaggcgaca agcgacctgc   7500
cgccacaaag aaggctggac aggctaagaa gaagaaagat tacaaagacg atgacgataa   7560
gggatccggc gcaacaaact tctctctgct gaaacaagcc ggagatgtcg aagagaatcc   7620
tggaccgacc gagtacaagc cacgtgcg cctgccacc cgcgacgacg tccccagggc   7680
cgtacgcacc ctcgccgccg cgttcgccga ctaccccgcc acgcgccaca ccgtcgatcc   7740
ggaccgccac atcgagcggg tcaccgagct gcaagaactc ttcctcacgc gcgtcgggct   7800
cgacatcggc aaggtgtggg tcgcggacga cggcgccgcg gtggcggtct ggaccacgcc   7860
ggagagcgtc gaagcgggg cggtgttcgc cgagatccgc ccgcgcatgg ccgagttgag   7920
cggttcccgg ctggccgcgc agcaacagat ggaaggcctc ctggcgccgc accggcccaa   7980
ggagcccgcg tggttcctgg ccaccgtcgg agtctcgccc gaccaccagg caagggtct   8040
gggcagcgcc gtcgtgctcc ccggagtgga ggcggccgag cgcgccgggg tgcccgcctt   8100
cctggagacc tccgcgcccc gcaacctccc ctttctacgag cgtcggct tcaccgtcac   8160
cgccgacgtc gaggtgcccg aaggaccgcg cacctggtgc atgacccgca agcccggtgc   8220
ctgaacgcgt taagtcgaca atcaacctct ggattacaaa atttgtgaaa gattgactgg   8280
tattcttaac tatgttgctc cttttacgct atgtggatac gctgctttaa tgcctttgta   8340
tcatgctatt gcttcccgta tggctttcat tttctcctcc ttgtataaat cctggttgct   8400
gtctctttat gaggagttgt ggcccgttgt caggcaacgt ggcgtggtgt gcactgtgtt   8460
tgctgacgca accccactg gttgggcat tgccaccacc tgtcagctcc tttccgggac   8520
tttcgctttc cccctcccta ttgccacggc ggaactcatc gccgcctgcc ttgcccgctg   8580
ctggacaggg gctcggctgt tgggcactga caattccgtg gtgttgtcgg ggaaatcatc   8640
gtcctttcct tggctgctcg cctgtgttgc cacctggatt ctgcgcggga cgtccttctg   8700
ctacgtccct tcggccctca atccagcgga ccttccttcc cgcggcctgc tgccggctct   8760
gcggcctctt ccgcgtcttc gccttcgccc tcagacgagt cggatctccc tttgggccgc   8820
ctccccgcgt cgactttaag accaatgact acaaggcag ctgtagatct tagccacttt   8880
ttaaaagaaa agggggact ggaagggcta attcactcc aacgaagaca agatctgctt   8940
tttgcttgta ctgggtctct ctggttagac cagatctgag cctgggagct ctctggctaa   9000
ctagggaacc cactgcttaa gcctcaataa agcttgcctt gagtgcttca agtagtgtgt   9060
gcccgtctgt tgtgtgactc tggtaactag agatccctca gacccttta gtcagtgtgg   9120
aaaatctcta gcagggcccg tttaaccccg ctgatcagcc tcgactgtgc cttctagttg   9180
ccagccatct gttgtttgcc cctccccgt gccttcttg accctggaag tgccactcc   9240
cactgtcctt tcctaataaa atgaggaaat tgcatcgcat tgtctgagta ggtgtcattc   9300
tattctgggg gtggggtgg gcaggacag caaggggga gattggaag acaatagcag   9360
gcatgctggg gatgcggtgg gctctatggc ttctgaggcg gaaagaacca gctgggctc   9420
tagggggtat ccccacgcgc cctgtagcgg cgcattaagc gcggcgggtg tggtggttac   9480
gcgcagcgtg accgctacac ttgccagcgc cctagcgccc gctcctttcg ctttcttccc   9540
ttcctttctc gccacgttcg ccggctttcc ccgtcaagct ctaaatcggg ggctcccttt   9600
```

```
agggttccga tttagtgctt tacggcacct cgaccccaaa aaacttgatt agggtgatgg    9660
ttcacgtagt gggccatcgc cctgatagac ggttttcgc cctttgacgt tggagtccac     9720
gttctttaat agtggactct tgttccaaac tggaacaaca ctcaacccta tctcggtcta    9780
ttcttttgat ttataaggga ttttgccgat ttcggcctat tggttaaaaa atgagctgat    9840
ttaacaaaaa tttaacgcga attaattctg tggaatgtgt gtcagttagg gtgtggaaag    9900
tccccaggct ccccagcagg cagaagtatg caaagcatgc atctcaatta gtcagcaacc    9960
aggtgtggaa agtccccagg ctccccagca ggcagaagta tgcaaagcat gcatctcaat   10020
tagtcagcaa ccatagtccc gcccctaact ccgcccatcc cgcccctaac tccgcccagt   10080
tccgcccatt ctccgcccca tggctgacta atttttttta tttatgcaga ggccgaggcc   10140
gcctctgcct ctgagctatt ccagaagtag tgaggaggct ttttggagg cctaggcttt    10200
tgcaaaagc tcccgggagc ttgtatatcc attttcggat ctgatcagca cgtgttgaca    10260
attaatcatc ggcatagtat atcggcatag tataatacga caaggtgagg aactaaacca   10320
tggccaagtt gaccagtgcc gttccggtgc tcaccgcgcg cgacgtcgcc ggagcggtcg    10380
agttctggac cgaccggctc gggttctccc gggacttcgt ggaggacgac ttcgccggtg    10440
tggtccggga cgacgtgacc ctgttcatca gcgcggtcca ggaccaggtg gtgccggaca    10500
acaccctggc ctgggtgtgg gtgcgcggcc tggacgagct gtacgccgag tggtcggagg    10560
tcgtgtccac gaacttccgg gacgcctccg ggcggccat gaccgagatc ggcgagcagc     10620
cgtgggggcg ggagttcgcc ctgcgcgacc cggccggcaa ctgcgtgcac ttcgtggccg    10680
aggagcagga ctgacacgtg ctacgagatt tcgattccac cgccgccttc tatgaaaggt    10740
tgggcttcgg aatcgttttc cgggacgccg gctggatgat cctccagcgc ggggatctca    10800
tgctggagtt cttcgcccac cccaacttgt ttattgcagc ttataatggt tacaaataaa    10860
gcaatagcat cacaaatttc acaaataaag cattttttc actgcattct agttgtggtt    10920
tgtccaaact catcaatgta tcttatcatg tctgtatacc gtcgacctct agctagagct    10980
tggcgtaatc atggtcatag ctgtttcctg tgtgaaattg ttatccgctc acaattccac    11040
acaacatacg agccggaagc ataaagtgta aagcctgggg tgcctaatga gtgagctaac    11100
tcacattaat tgcgttgcgc tcactgcccg ctttccagtc gggaaacctg tcgtgccagc    11160
tgcattaatg aatcggccaa cgcgcgggga gaggcggttt gcgtattggg cgctcttccg    11220
cttcctcgct cactgactcg ctgcgctcgg tcgttcggct gcggcgagcg gtatcagctc    11280
actcaaaggc ggtaatacgg ttatccacag aatcagggga taacgcagga aagaacatgt    11340
gagcaaaagg ccagcaaaag gccaggaacc gtaaaaaggc cgcgttgctg gcgtttttcc    11400
ataggctccg cccccctgac gagcatcaca aaaatcgacg ctcaagtcag aggtggcgaa    11460
acccgacagg actataaaga taccaggcgt ttccccctgg aagctccctc gtgcgctctc    11520
ctgttccgac cctgccgctt accggatacc tgtccgcctt ctcccttcg ggaagcgtgg     11580
cgctttctca tagctcacgc tgtaggtatc tcagttcggt gtaggtcgtt cgctccaagc    11640
tgggctgtgt gcacgaaccc cccgttcagc ccgaccgctg cgccttatcc ggtaactatc    11700
gtcttgagtc caacccggta agacacgact tatcgccact ggcagcagcc actggtaaca    11760
ggattagcag agcgaggtat gtaggcggtg ctacagagtt cttgaagtgg tggcctaact    11820
acggctacac tagaagaaca gtatttggta tctgcgctct gctgaagcca gttaccttcg    11880
gaaaaagagt tggtagctct tgatccggca aacaaaccac cgctggtagc ggtggttttt    11940
ttgtttgcaa gcagcagatt acgcgcagaa aaaaaggatc tcaagaagat cctttgatct    12000
tttctacggg gtctgacgct cagtggaacg aaaactcacg ttaagggatt ttggtcatga    12060
gattatcaaa aaggatcttc acctagatcc ttttaaatta aaaatgaagt tttaaatcaa    12120
tctaaagtat atatgagtaa acttggtctg acagttacca atgcttaatc agtgaggcac    12180
ctatctcagc gatctgtcta tttcgttcat ccatagttgc ctgactcccc gtcgtgtaga    12240
taactacgat acgggagggc ttaccatctg gccccagtgc tgcaatgata ccgcgagacc    12300
cacgctcacc ggctccagat ttatcagcaa taaaccagcc agccggaagg gccgagcgca    12360
gaagtggtcc tgcaacttta tccgcctcca tccagtctat taattgttgc cgggaagcta    12420
gagtaagtag ttcgccagtt aatagtttgc gcaacgttgt tgccattgct acaggcatcg    12480
tggtgtcacg ctcgtcgttt ggtatggctt cattcagctc cggttcccaa cgatcaaggc    12540
gagttacatg atccccccatg ttgtgcaaaa aagcggttag ctccttcggt cctccgatcg   12600
ttgtcagaag taagttggcc gcagtgttat cactcatggt tatggcagca ctgcataatt    12660
ctcttactgt catgccatcc gtaagatgct tttctgtgac tggtgagtac tcaaccaagt    12720
cattctgaga atagtgtatg cggcgaccga gttgctcttg cccggcgtca tacgggata     12780
ataccgcgcc acatagcaga actttaaaag tgctcatcat tggaaaacgt tcttcggggc    12840
gaaaactctc aaggatctta ccgctgttga tccagttc gatgtaaccc actcgtgcac      12900
ccaactgatc ttcagcatct tttactttca ccagcgtttc tgggtgagca aaaacaggaa    12960
ggcaaaatgc cgcaaaaaag gaataagggc gacacggaa atgttgaata ctcatactct     13020
tccttttca atattattga agcatttatc agggttattg tctcatgagc ggatacatat     13080
ttgaatgtat ttagaaaaat aaacaaatag gggttccgcg cacatttccc cgaaaagtgc    13140
cacctgac                                                            13148

SEQ ID NO: 20         moltype = RNA   length = 53
FEATURE               Location/Qualifiers
misc_feature          1..53
                      note = Minizyme Mz
source                1..53
                      mol_type = other RNA
                      organism = synthetic construct
SEQUENCE: 20
tgtttcgcct gatgagtttt cgaaacgatt ttctctcaaa tcgtcgcgaa aca             53
```

```
SEQ ID NO: 21          moltype = RNA  length = 53
FEATURE                Location/Qualifiers
misc_feature           1..53
                       note = Minizyme Mzwk
source                 1..53
                       mol_type = other RNA
                       organism = synthetic construct
SEQUENCE: 21
tgtttcgcct gatgagtttt cgaaacgatt ttctctcaaa tcgtggcgaa aca          53
```

INDUCIBLE CRISPR SYSTEM EXPRESSION AND APPLICATIONS THEREOF

CROSS-REFERENCE TO RELATED APPLICATION

The present application is a continuation application of U.S. application Ser. No. 17/491,738, filed Oct. 1, 2021, the disclosure of which is hereby incorporated by reference in its entirety, including all figures, tables, drawings, and sequences.

GOVERNMENT SUPPORT

This invention was made with government support under W81XWH1810662 awarded by the Department of Defense. The government has certain rights in the invention.

SEQUENCE LISTING

The Sequence Listing for this application is labeled SeqList-27Mar23.xml" was created on Mar. 27, 2023, and is 54,527 bytes in size. The entire contents are incorporated herein by reference.

BACKGROUND OF THE INVENTION

CRISPR (Clustered, Regularly Interspaced, Short Palindromic Repeats) refers to a family of genes in bacteria and archaea. These organisms defend against infections by phages and plasmids by utilizing CRISPR-derived RNA and various Cas (CRISPR-associated) proteins. Cas proteins are endonucleases that are guided by an RNA to induce site-specific cleavage of double stranded nucleic acids, rendering the target gene inoperable. Because of its versatility and precision, "CRISPR-Cas9" is the most frequently employed CRISPR system for, e.g., gene editing, epigenetic modulation, and transcriptional control. The core components of the "CRISPR-Cas9" systems are Cas9 and guide RNA (gRNA). gRNA "guides" Cas9 to a target sequence by possessing a nucleotide sequence about 20 bp that is complementary to a region in the target sequence. The sequence of gRNAs can be tailored to virtually any target sequence, and screening of gRNA sequences can identify an optimal gRNA sequence for a given target gene.

Genetic expression of CRISPR systems known to date is not fully controllable. More specifically, known CRISPR systems produce gRNAs from Pol III-based promoters, which are unregulated promoters that allow for constitutive transcription of gRNA genes, often resulting in overexpression of gRNAs. This can lead to off-target effects that can cause mutations and/or loss of gene function at untargeted genomic sites, which can lead to various problems such as carcinogenesis or toxicity. Such problem persists even after CRISPR systems are optimized through gRNA library screening and modifications to Cas proteins.

A number of studies have reported attempts to control Cas9 expression with various drugs, either transcriptionally or post-transcriptionally. Examples include inducible Tet-ON and Tet-OFF Pol II promoters for temporal control of Cas9 expression. See, e.g., Gonzalez, F. et al., An iCRISPR Platform for Rapid, Multiplexable, and Inducible Genome Editing in Human Pluripotent Stem Cells, Cell Stem Cell, 15(2):215-26 (2014). Others have used Cre-based transcriptional regulation. See, e.g., St-Onge, L. et al., Temporal Control of the Cre Recombinase in Transgenic Mice by a Tetracycline Responsive Promoter, Nucleic Acids Res., 24(19): 3875-7 (1996). However, Pol III-mediated gRNA expression is still constitutive in these approaches, and only Pol II-mediated Cas9 expression is inducible. Since there are no chimeric Pol II-Pol III promoters, Pol II and Pol III promoters require separate transcription units and different termination signals. This makes coordinated control of gRNA and Cas9 expression difficult.

Furthermore, a drug-inducible system is not always practical especially in a therapeutic setting, as every cell harboring the CRISPR system would express Cas9 upon administration of the drug, and constitutively express gRNA, even if such expression is not necessary or can be even harmful. In such cases, it is highly desirable to require conditional or cell-type specific expression of CRISPR systems.

One therapeutic area in which CRISPR systems show great potential is HIV/AIDS. Cas9 has been used in preventing viruses from manipulating hosts' DNA. While the advent of combination antiretroviral therapy ("cART") has led to a dramatic decline in morbidity and mortality from HIV/AIDS, cART is still unable to eradicate HIV due to established HIV reservoirs in cells. HIV replication persists even in the presence of suppressive cART and continues to produce low levels of inflammatory cytokines and viral proteins, which are some of the primary causes of non-AIDS comorbidities of HIV. Various cell types that can serve as HIV reservoirs include, but are not limited to, resting CD4+ T-cells, macrophages, astrocytes, and microglia. One crucial limitation of CRISPR-based targeting of HIV is the ability of HIV to mutate the sites targeted by CRISPR systems to escape inactivation. Similar limitations have also been observed with other types of gene therapy approaches targeting the viral RNA/genome. To prevent this HIV escape, alternative and more attractive targets for CRISPR systems are the host's cellular cofactors that play critical roles in HIV's life cycle. Targeting of cellular cofactors makes viral escape through mutations irrelevant, but it does not come without challenges: Uncontrolled silencing of cellular factors is risky, as cellular factors also have roles in the host cell's homeostasis. Therefore, in order to achieve a functional cure or effectuate long-term suppression, a successful CRISPR-based therapy should have a mechanism to conditionally limit the activity of CRISPR systems.

An example of a CRISPR system that is inducible by the presence of HIV virus was reported by Kaminski et al. Their CRISPR system expressed Cas9 from a truncated HIV long terminal repeat (LTR) in response to HIV-1 TAT present in cells infected by HIV. See Kaminski, R. et al., Negative Feedback Regulation of HIV-1 by Gene Editing Strategy. Sci Rep. 6:31527 (2016). In this system, however, only Cas9 expression was inducible by HIV while the gRNAs were expressed from a separate and constitutive Pol III promoter. These gRNAs can inadvertently trigger transcriptional gene silencing due to partial hybridization with other cellular RNAs or regions of genes that are not intended therapeutic targets. As the long-term effects of such constitutive expression of gRNA are unknown, it is desirable to have a CRISPR system whose expression of both Cas and guide sequences is controllable. To date, no such system has been reported.

BRIEF SUMMARY OF THE INVENTION

The present invention relates to an inducible CRISPR system for controlling expression of a CRISPR complex that functions to silence or otherwise edit target gene expression. CRISPR complex, whose main components are a Cas protein and a guide sequence, is expressed from a construct comprising an inducible fusion promoter comprising a suitable promoter operatively associated with an inducible element. The CRISPR complex is preferably produced only in the presence of an inducer that is specific for the inducible element. Advantageously, the present invention provides a CRISPR system whose expression of both Cas and a guide sequence is inducible and driven from the same promoter.

In one aspect, the present invention provides a CRISPR system whose expression of two or more elements of the CRISPR system is inducible with an inducer. The inducible CRISPR system comprises an inducible fusion promoter comprising a suitable promoter operatively associated with an inducible element to drive expression of the two or more elements. In some embodiments, the inducible element is responsive to a tissue specific, viral specific, cellular specific, or engineered transcription factor. In one embodiment, the inducible element is responsive to a viral specific transcription factor. In a specific embodiment, the inducible fusion promoter comprises a Pol II promoter operatively associated with an HIV-1 LTR containing the TAR sequences and is inducible by HIV-1 TAT.

In a second aspect, the present invention provides an inducible CRISPR system whose expression of both a guide sequence and Cas is driven by an inducible fusion promoter. Expression of both the guide sequence and Cas is driven by an inducible fusion promoter comprising a suitable promoter that is operatively associated with an inducible element, which in turn is inducible by an inducer. In some embodiments, the inducible element is responsive to a tissue specific, viral specific, cellular specific, or engineered transcription factor. In yet a further embodiment, the inducible element is responsive to a viral specific transcription factor. In a specific embodiment, the inducible fusion promoter comprises a Pol II promoter operatively associated with the inducible element which is an HIV-1 LTR promoter containing the TAR sequences, inducible by HIV-1 TAT.

In a third aspect, the present invention provides an inducible CRISPR system further comprising a catalyzing RNA. In one embodiment the catalyzing RNA is incorporated into the inducible CRISPR system construct immediately upstream of the guide sequence. In a further embodiment a second catalyzing RNA is incorporated into the inducible CRISPR system construct downstream of the guide sequence. In one embodiment the catalyzing RNA is a ribozyme. In a further embodiment, the ribozyme is a cis-cleaving ribozyme. In a yet further embodiment, the cis-cleaving ribozyme is a modified hammerhead ribozyme that has lower RNA cleavage efficiency than its unmodified counterpart.

In a fourth aspect, the present invention provides for controllable expression of two or more elements of the inducible CRISPR system in cells that contain an inducer that is specific for the inducible element. In a further embodiment, the cells naturally express the inducer. In another embodiment, the cells are viral infected cells that express the inducer. In yet another embodiment, the cells are cells harboring HIV-1 which produces the inducer such as TAT. In a further embodiment, the cells are cells transfected with a vector that expresses the inducer. In another embodiment, the cells are cells transfected with a vector expressing TAT.

In a fifth aspect, the present invention provides methods for silencing or otherwise editing a target gene in a cell and treating one or more diseases caused by the expression of the gene by using an inducible CRISPR system. In one embodiment, the method involves introducing into a cell the inducible CRISPR system to cause a silencing or otherwise alteration of the target gene.

In a sixth aspect, the present invention provides for a method of enhancing the effects of the inducible CRISPR system by introducing a catalyzing RNA into the construct. In one embodiment the catalyzing RNA is a ribozyme. In a further embodiment the ribozyme is a cis-cleaving ribozyme that has been modified to lower its RNA cleavage efficiency.

In a seventh aspect, the present invention provides methods for inducing expression of a CRISPR system in a transient as well as in a stable long-term setting.

The present invention provides an inducible CRISPR system that is useful, for example, for CRISPR-based gene therapy. The present invention is particularly advantageous in that it addresses the safety concerns of off-target effects that are often associated with CRISPR systems by providing a construct and method to control the expression of CRISPR systems including the guide sequence. These advantages thus enhance the utility of the present invention in the clinical setting.

The methods and systems described herein have pharmaceutical, medical, and veterinary applications, as well as be useful in scientific research and methodologies, as would be identifiable by a skilled person upon reading the present disclosure.

Figure 2A:
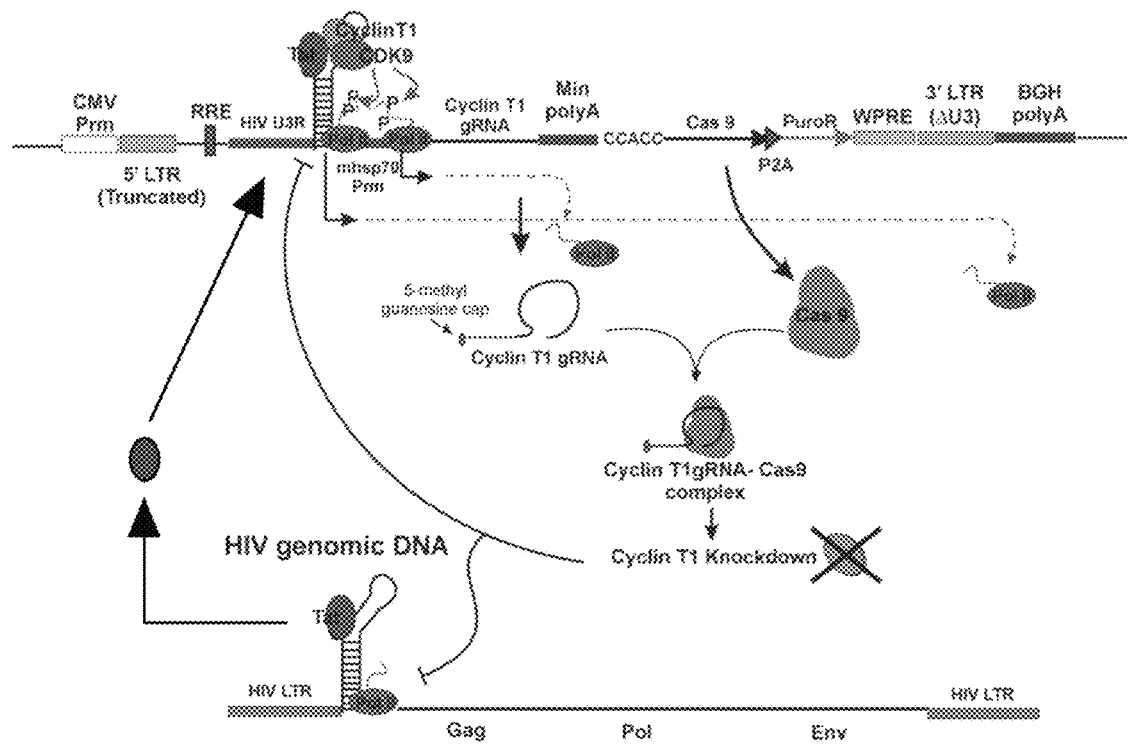
FIG. 2A is a schematic representation of an embodiment of an inducible CRISPR system of the present invention in pLentiCRISPR v2 plasmid (not drawn to scale), and its mechanism to self-limit its expression.
Figure 2B:
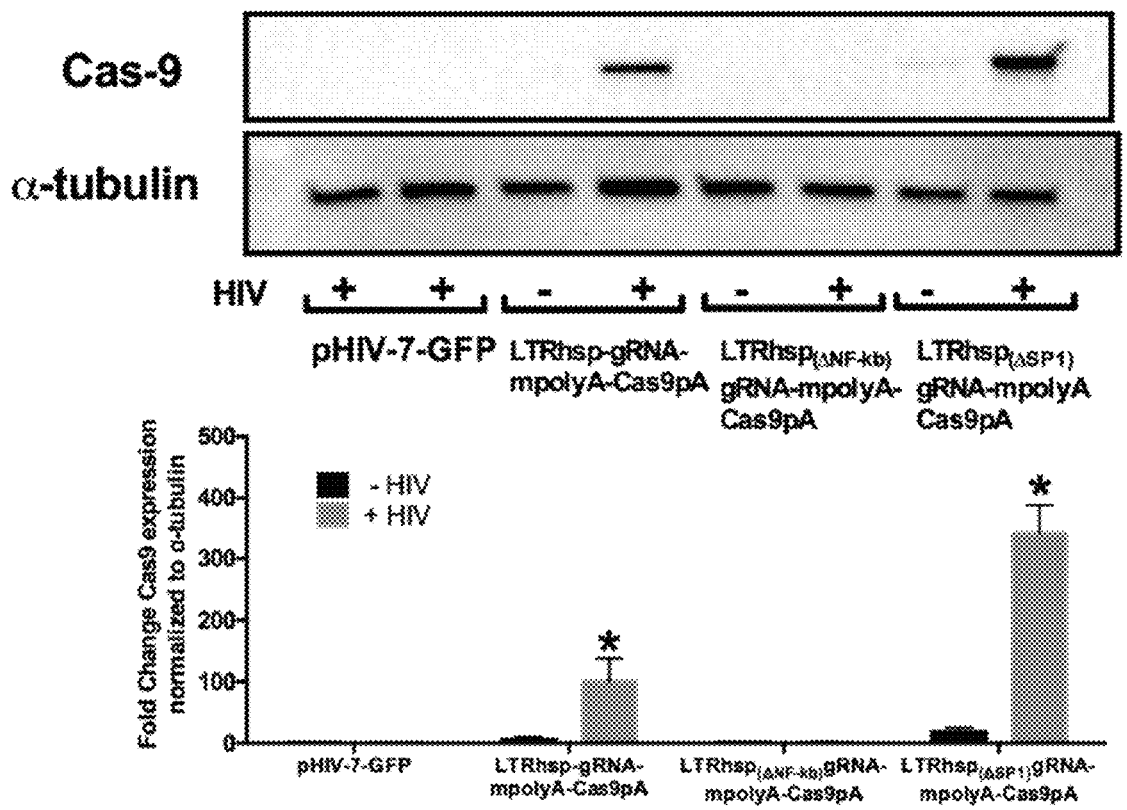
FIG. 2B shows results of Western blot analysis normalized to α-tubulin and a graph comparing the LTRhsp-gRNA-mpolyA-Cas9pA construct of the present invention with its NF-κβ and SP1 deletion mutants, LTR(ΔNF-κβ)-gRNA-mpolyA-Cas9pA and LTR(ΔSP1)-gRNA-mpolyA-Cas9pA respectively, for their Cas9 expression levels 72-hours post-transfection in HIV-infected ("+HIV") and uninfected ("−HIV") HeLa-CD4 cells. Results of LTRhsp-gRNA-mpolyA-Cas9pA demonstrate that its expression is inducible with HIV, while the two mutants either failed to produce Cas (in the case of NF-κβ deletion mutant) or exhibited some Cas9 expression in the absence of HIV (in the case of SP1 deletion mutant). n=mean+/−SEM from 3 independent experiments. *=significant from control.
Figure 2C:
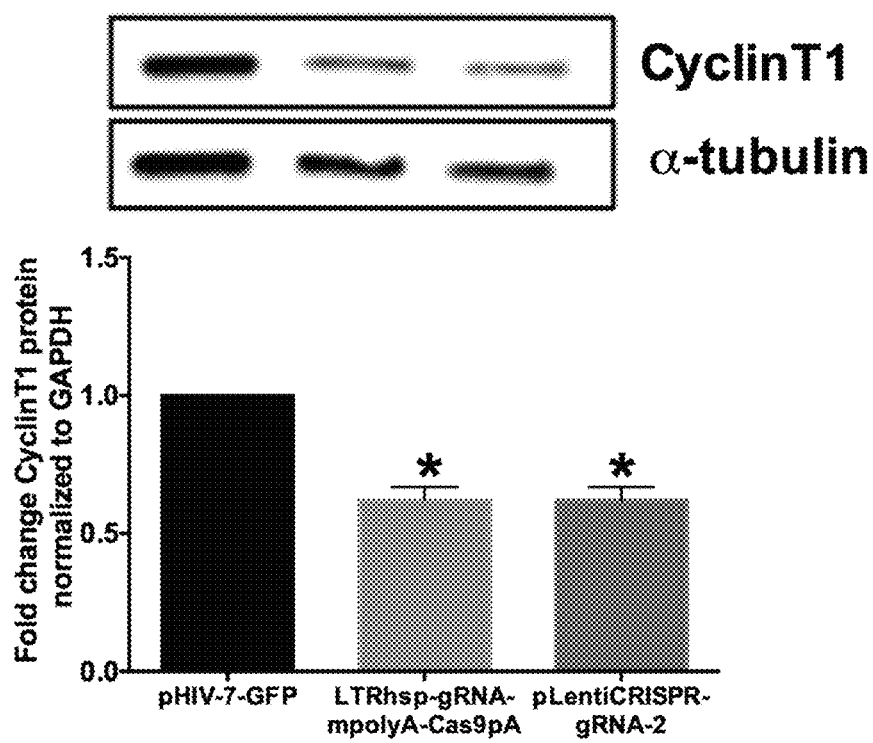

FIG. 2C shows results of Western blot analysis normalized to α-tubulin and a graph of Cyclin T1 suppression levels 6-days post-transfection in HIV-infected HeLa-CD4 cells transfected with the LTRhsp-gRNA-mpolyA-Cas9pA construct according to the present invention and with the pLentiCRISPR-gRNA-2 construct that constitutively expresses gRNA-2 and Cas9. The results indicate that both constructs achieved suppression of Cyclin T1 in HIV-infected HeLa-CD4 cells compared to the control (pHIV-7-GFP). n=mean+/−SEM from 3 independent experiments. *=significant from control (p<0.05).

Figure 2D:
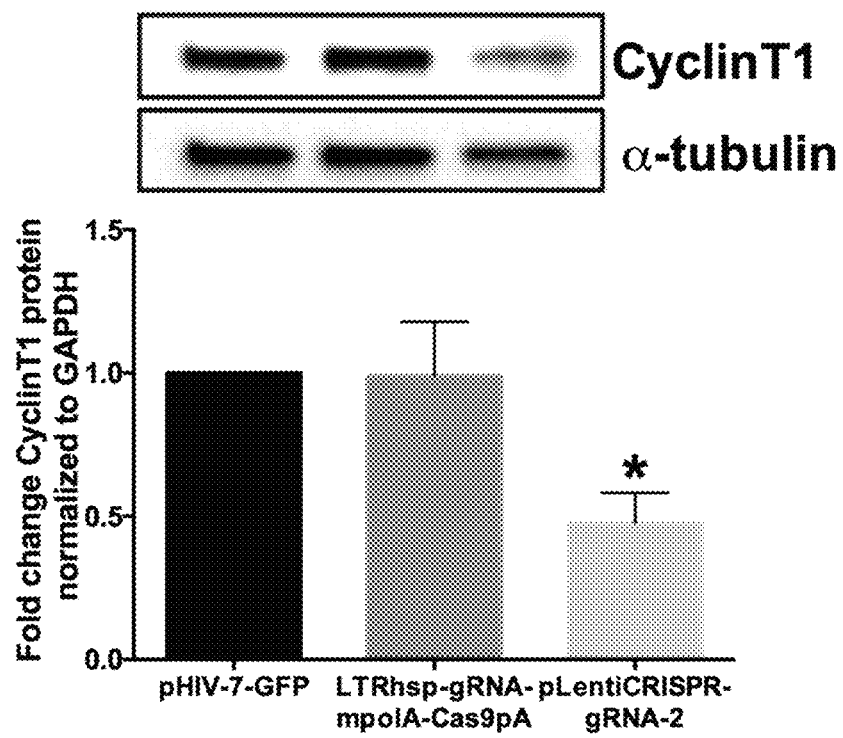

FIG. 2D shows results of Western blot analysis normalized to α-tubulin and a graph of Cyclin T1 suppression levels 6-days post-transfection in uninfected HeLa-CD4 cells transfected with the LTRhsp-gRNA-mpolyA-Cas9pA construct according to the present invention and with the pLentiCRISPR-gRNA-2 construct that constitutively expresses gRNA-2 and Cas9. Unlike the results shown in FIG. 2C, only the constitutive pLentiCRISPR-gRNA-2 exhibited Cyclin T1 suppression in the uninfected cells, demonstrating the HIV-inducibility of the CRISPR system of the invention. n=mean+/−SEM from 3 independent experiments. *=significant from control (p<0.05).

Figure 2E:
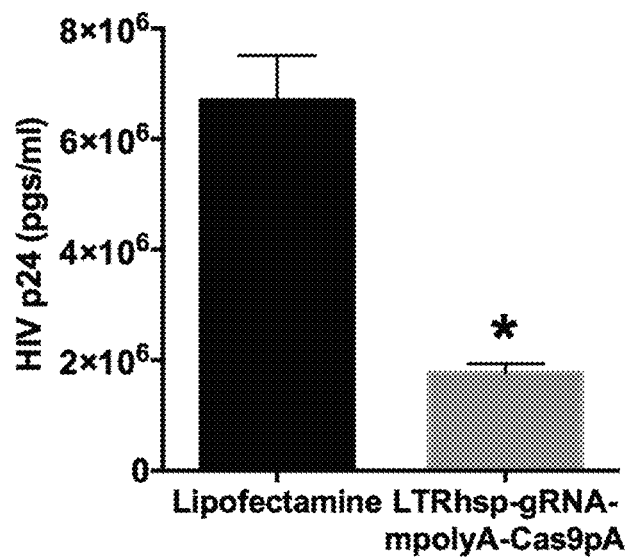

FIG. 2E is a graph showing the HIV p24 levels on day 6 post-infection in HIV-infected HeLa-CD4 cells transfected once with LTRhsp-gRNA-mpolyA-Cas9pA according to the present invention. The results indicate that LTRhsp-gRNA-mpolyA-Cas9pA achieved a statistically significant suppression of HIV p24 levels compared to the control. n=mean+/−SEM from 3 independent experiments. *=significant from control (p<0.05).

Figure 3A:
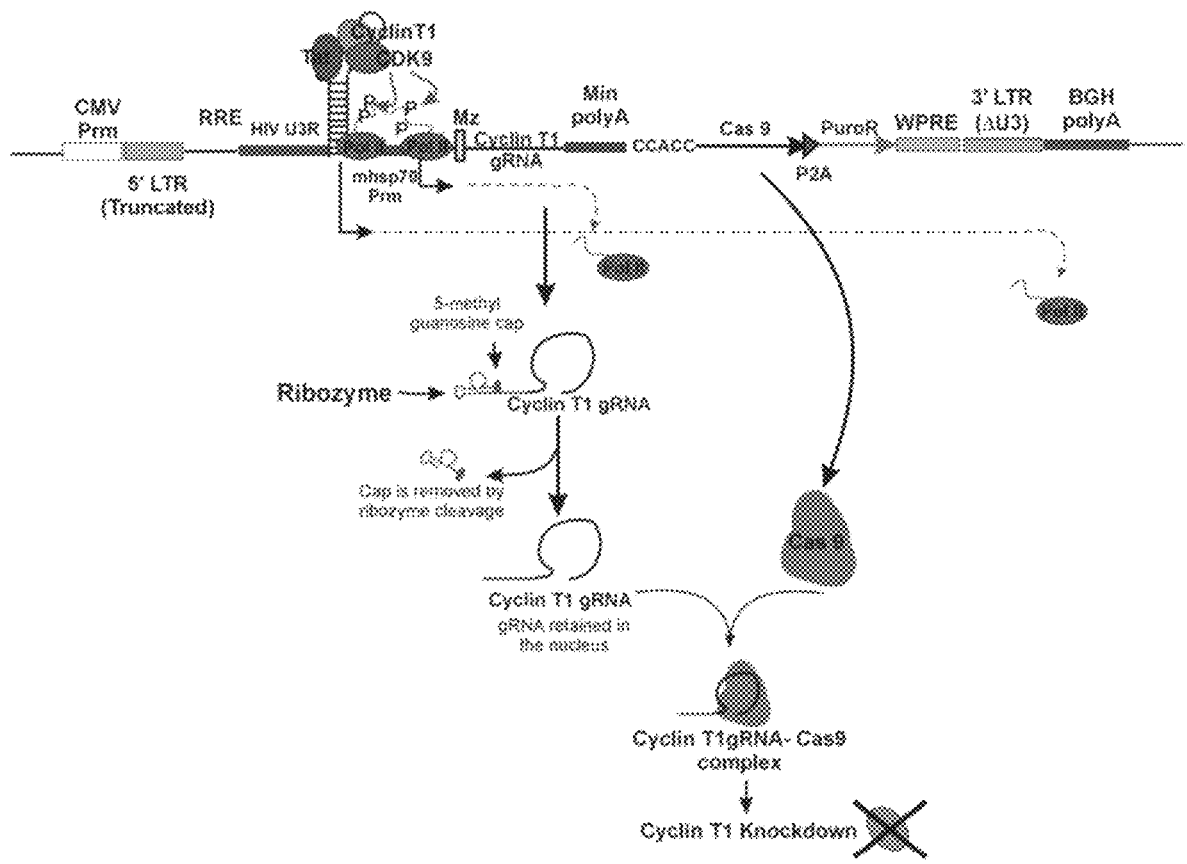

FIG. 3A shows a schematic representation of the effects of the minizyme-embedded CRISPR system according to the present invention. Embedding a cis-acting minizyme (labeled "Mz") immediately upstream of the Cyclin T1 gRNA such that it cleaves the 5' cap of the gRNA transcripts results in the retention of the gRNA in the nucleus, preventing the gRNA from being exported from the nucleus to the cytoplasm.

Figure 3B:
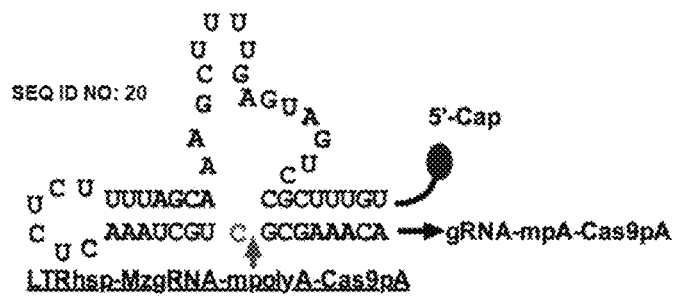
Figure 3B:
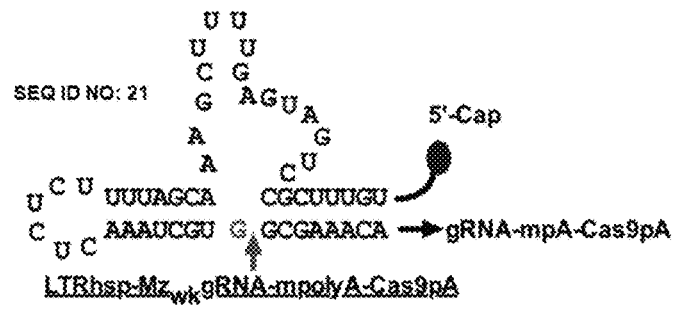

FIG. 3B shows schematic representations of minizyme-embedded variants (LTRhspMzgRNA-mpolyA-Cas9pA and LTRhspMz$_{wk}$gRNA-mpolyA-Cas9pA) and their cleavage sites (indicated with upward pointing arrows) upstream of the gRNA for removal of the 5'-cap.

Figure 3C:
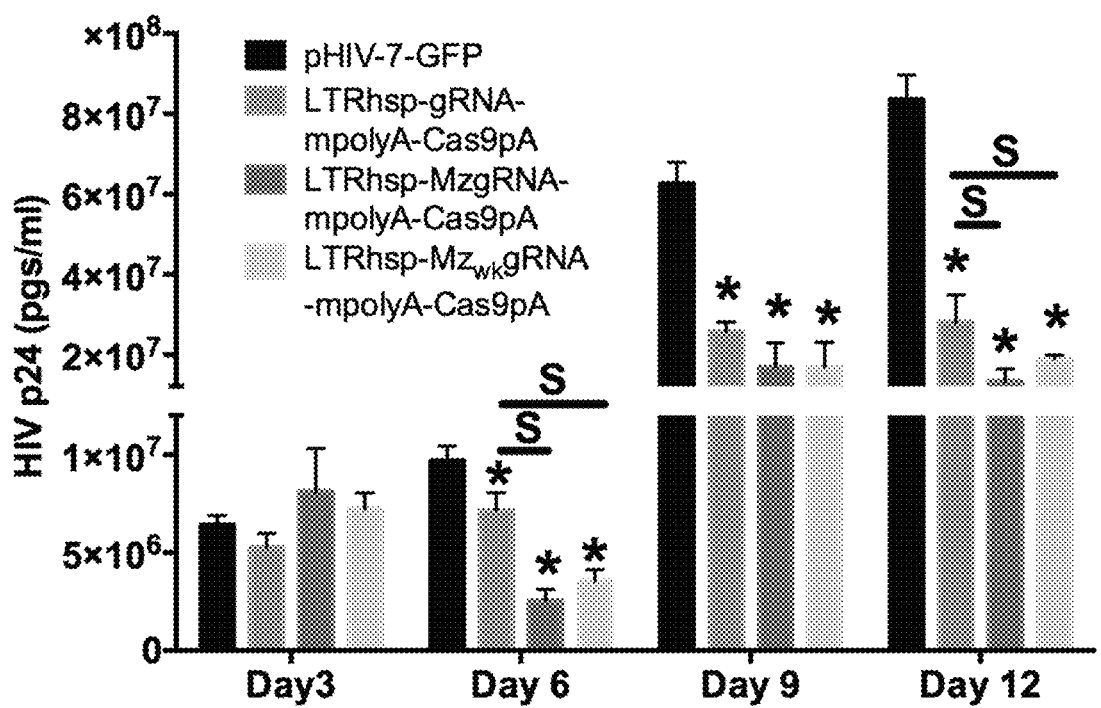

FIG. 3C is a graph showing the effects of the two minizyme-embedded variants, LTRhspMzgRNA-mpolyA-Cas9pA and LTRhspMz$_{wk}$gRNA-mpolyA-Cas9pA, on the HIV p24 viral antigen levels in HIV-infected HeLa-CD4 cells. Transfection with LTRhsp-gRNA-mpolyA-Cas9 pA was used for comparison. Both minizyme-embedded variants demonstrated improved HIV p24 suppression compared to LTRhsp-gRNA-mpolyA-Cas9pA. n=mean+/−SEM from 3 independent experiments. *=significant from control. S=significant from each other (p<0.05).

Figure 3D:
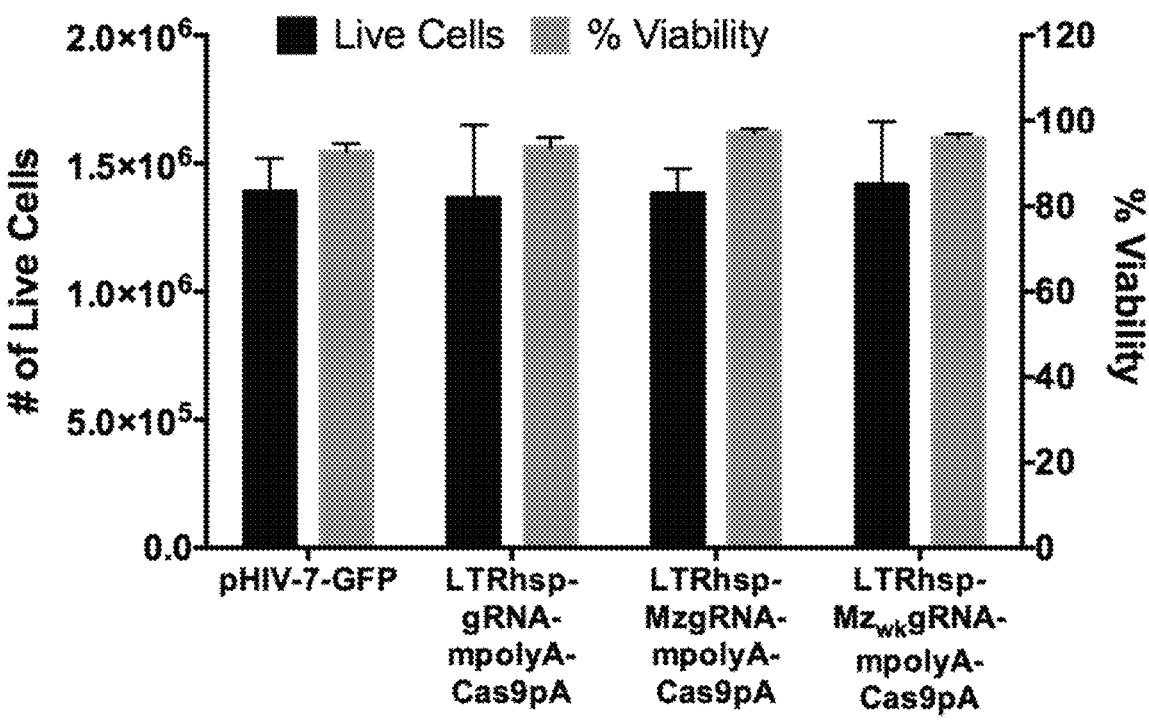

FIG. 3D is a graph showing the number of live cells and viability of the HIV-infected HeLa-CD4 cells transfected with the two minizyme-embedded variants (LTRhspMzgRNA-mpolyA-Cas9pA and LTRhspMz$_{wk}$gRNA-mpolyA-Cas9pA) and with LTRhsp-gRNA-mpolyA-Cas9pA. Following 12 days post-transfection, LTRhsp-gRNAmpolyA-Cas9pA and the two variants did not adversely affect cell viability and demonstrated similar live cell counts compared to the control. n=mean+/−SEM from 3 independent experiments.

Figure 4A:
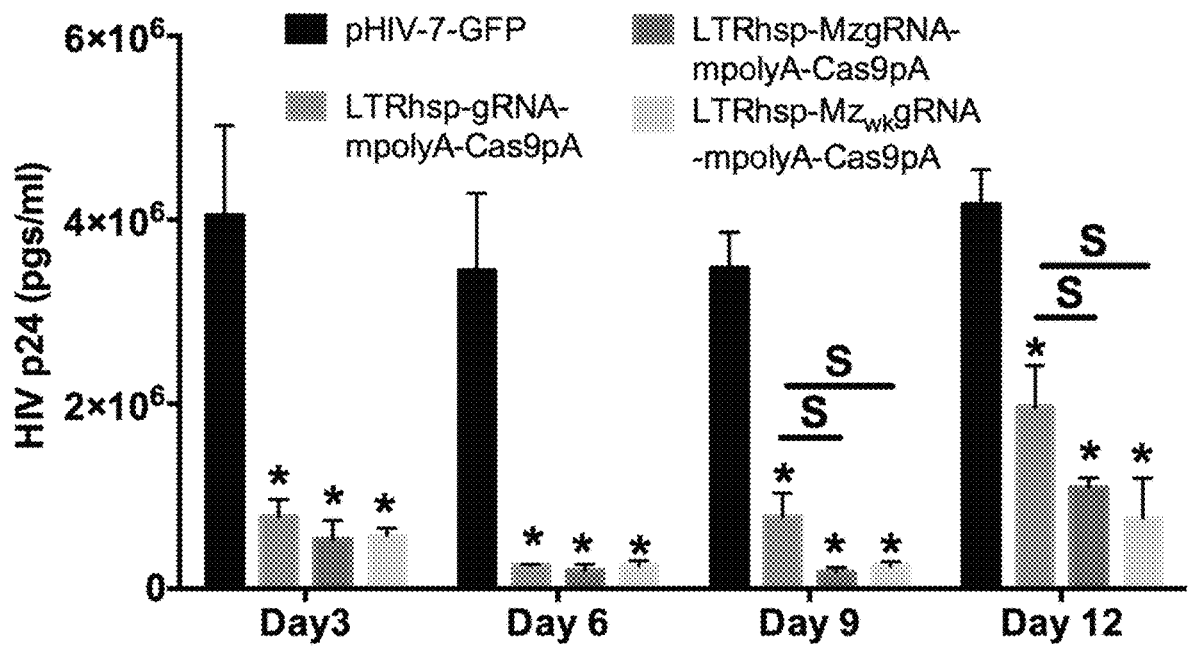

FIG. 4A is a graph demonstrating prolonged and sustained HIV suppression in CEM T-cells transfected with the HIV-inducible CRISPR systems of the present invention, LTRhsp-gRNA-mpolyA-Cas9pA, LTRhspMzgRNA-mpolyA-Cas9pA, and LTRhspMz$_{wk}$gRNA-mpolyA-Cas9pA. All three systems demonstrated HIV suppression that persisted up to 12 days post-electroporation. LTRhsp-gRNA-mpolyA-Cas9pA demonstrated maximum suppression by Day 6 followed by a progressive increase in viral output on days 9 and 12 with a 53% HIV suppression observed on Day 12. Both minizyme-embedded variants demonstrated better efficacy of about 95% suppression on day 9 as well as a more sustained HIV suppression up to day 12 (about 85%). n=mean+/−SEM from 4 independent experiments. *=significant from control. S=significant from each other (p<0.05).

Figure 4B:
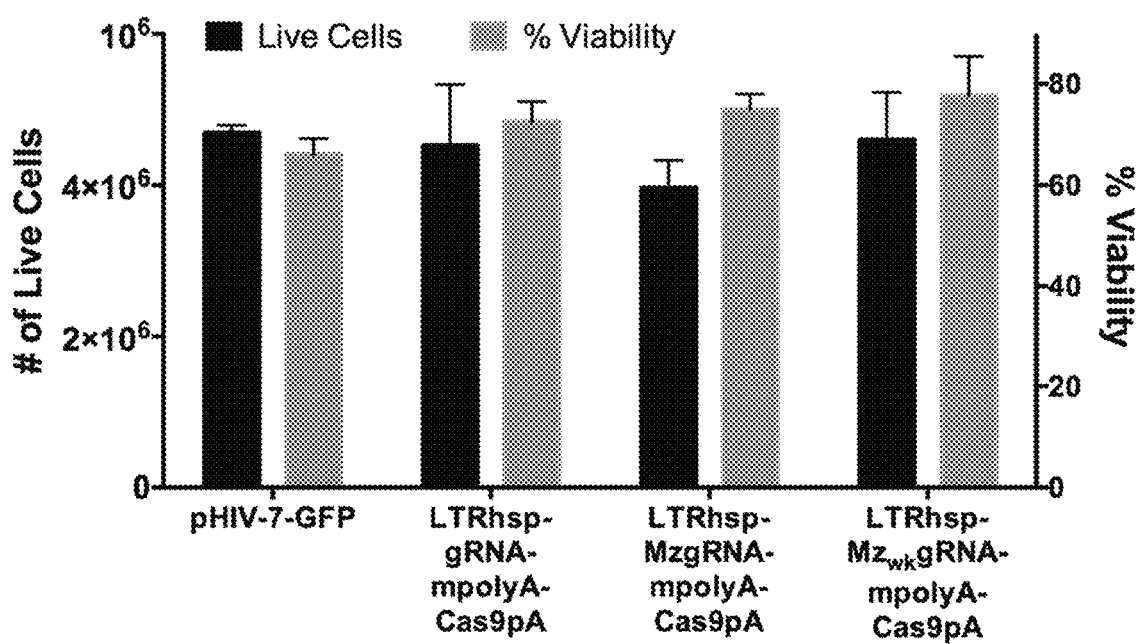

FIG. 4B is a graph showing the number of live cells and viability of HIV-infected CEM T-cells transfected with the HIV-inducible CRISPR systems of the present invention, LTRhsp-gRNA-mpolyA-Cas9pA, LTRhspMzgRNA-mpolyA-Cas9pA, and LTRhspMz$_{wk}$gRNA-mpolyA-Cas9pA. Compared to the control, all three systems did not adversely affect % cell viability or number of live cells. n=mean+/−SEM from 4 independent experiments.

Figure 5:
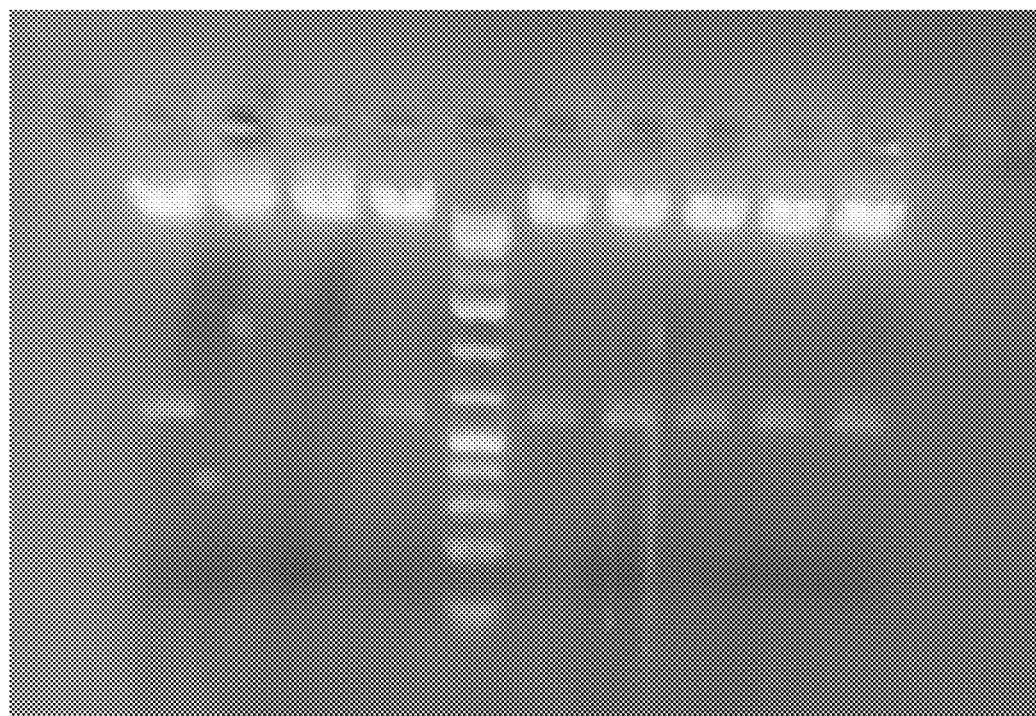

FIG. 5 shows results of gel electrophoresis analysis of the ribozyme-embedded constructs LTRhsp-MzgRNA-mpolyA-Cas9pA and LTRhsp-Mz$_{wk}$gRNA-mpolyA-Cas9pA. Lanes 1-4 show screening of LTRhsp-MzgRNA-mpolyA-Cas9pA clones by restriction digestion with KpnI and XbaI. Lane 5 is 1 kb DNA ladder. Lanes 6-10 are screening of LTRhsp-Mz$_{wk}$gRNA-mpolyA-Cas9pA again after restriction digestion with KpnI and XbaI. Lanes 1, 4, 6-10 had the required size fragments.

BRIEF DESCRIPTION OF THE SEQUENCES

SEQ ID NO: 1 is a 5' primer containing a KpnI site for an inducible fusion promoter according to the present invention.

SEQ ID NO: 2 is a 3'primer for an inducible fusion promoter according to the present invention.

SEQ ID NO: 3 is a 5' primer for a gRNA.

SEQ ID NO: 4 is a 3' primer for a gRNA.

SEQ ID NO: 5 is a 5' primer for a minimal polyadenylation (mpolyA) signal sequence.

SEQ ID NO: 6 is a 3' primer containing a XbaI site for a minimal polyadenylation (mpolyA) signal sequence.

SEQ ID NO: 7 is a 3' primer containing a EcoR1 site for an inducible fusion promoter according to the present invention.

SEQ ID NO: 8 is a 5' primer for a fragment containing a partial modified ribozyme (Mz).

SEQ ID NO: 9 is a 5' primer containing an EcoR1 site for a fragment containing full modified ribozymes (Mz or Mz$_{wk}$).

SEQ ID NO: 10 is a 5' primer for a fragment containing a partial modified ribozyme (Mz$_{wk}$).

SEQ ID NO: 11 is a nucleotide sequence of HIV-1 LTR including TAR according to the present invention.

SEQ ID NO: 12 is a nucleotide sequence of minimal *Drosophila* hsp70 promoter according to the present invention.

SEQ ID NO: 13 is a nucleotide sequence of a guide region of Cyclin T1 gRNA-1.

SEQ ID NO: 14 is a nucleotide sequence of a guide region of Cyclin T1 gRNA-2. SEQ ID NO: 15 is a nucleotide sequence of a guide region of Cyclin T1 gRNA-3.

SEQ ID NO: 16 is a nucleotide sequence of a modified ribozyme designated as Mz.

SEQ ID NO: 17 is a nucleotide sequence of a modified ribozyme designated as $Mz_{wk}$.

SEQ ID NO: 18 is a nucleotide sequence of an inducible CRISPR system according to the present invention designated as LTRhsp-gRNA-mpolyA-Cas9pA.

SEQ ID NO: 19 is a nucleotide sequence of an inducible CRISPR system according to the present invention designated as LTRhsp-MzgRNA-mpolyA-Cas9pA.

SEQ ID NO: 20 is an RNA nucleotide sequence of a modified ribozyme designated as Mz.

SEQ ID NO: 21 is an RNA nucleotide sequence of a modified ribozyme designated as $Mz_{wk}$.

DETAILED DESCRIPTION OF THE INVENTION

The present invention relates to an inducible CRISPR system for controlling expression with an inducible fusion promoter comprising a promoter operatively associated with an inducible element. Preferably, the inducible CRISPR system is induced only in the presence of an inducer that is specific for the inducible element. The invention is useful for silencing or otherwise altering gene expression using a CRISPR system in a controllable manner.

"CRISPR system" refers collectively to elements encoding, involved in the expression of, or directing the activity of, a CRISPR complex, including but not limited to nucleic acid sequences encoding a Cas gene, a guide sequence, and other sequences operatively associated with the CRISPR locus. CRISPR systems according to the present invention may be prepared by utilizing methods and techniques known to those skilled in the art. Example methods and techniques include, but are not limited to, polymerase chain reaction (PCR) or reverse transcription PCR (RT-PCR), digestion with restriction enzymes, ligation of two or more nucleic acid sequences, and combinations thereof. In some embodiments, one or more elements of a CRISPR system may be derived from Types I, II, III, IV, V, and/or VI CRISPR systems. Type I, II, and V function to cleave DNA, Type VI can edit RNA, and Type III edits both DNA and RNA. In other embodiments, one or more elements of a CRISPR system is derived from a particular organism comprising an endogenous CRISPR system, such as *Streptococcus pyogenes*. Due to its versatility as well as relative ease in silencing or otherwise editing, CRISPR technology has been utilized and suggested in various research and clinical settings. Thus, a person skilled in the art would appreciate that the present invention has various uses in areas including but not limited to genome editing, epigenome editing, gene screening, DNA/mRNA imaging, diagnostics, immunoprecipitation, transcriptional activation and suppression, and therapeutic applications.

The inducible CRISPR system of the present invention comprises a nucleotide sequence encoding a Cas. Cas (CRISPR-associated protein) is an endonuclease that catalyzes site-specific deletion or editing of a target sequence. In one embodiment, the Cas protein is Cas9 (also called Cas5, Csn1, or Csx12). It is within the purview of the present invention that a skilled artisan can identify and/or modify a Cas protein or associated sequences. In one embodiment, a translation initiation site may be provided upstream of a Cas sequence in order to facilitate translation of Cas transcript. For example, a strong eukaryotic translation initiation site (CCACC) can be provided upstream of Cas9 to ensure that the first ATG after this sequence is used for translation initiation. In some embodiments, a Cas protein is genetically modified to have a eukaryotic nuclear localization signal, particularly, a nuclear localization signal that is optimized for the host eukaryotic cell. In another embodiment, the Cas gene is genetically optimized for expression in a host cell, for example, by codon optimization. In other embodiments, modifications to the Cas gene inactivate its cleavage activity such that binding of the mutant Cas either activates or represses the target gene expression.

The inducible CRISPR system of the present invention further comprises a guide sequence. "Guide sequence" as used herein is any nucleic acid sequence comprising a guide (or spacer) region, often about 20 bp in length, having sufficient complementarity with a target sequence to hybridize with the target sequence and directing sequence-specific binding of a CRISPR complex to the target genome. A guide sequence may comprise a guide region (or alternatively called a spacer region) which is complementary to a target sequence and a scaffold region necessary for binding to Cas. A CRISPR complex comprises at least one Cas and a guide sequence that form a complex. Typically, formation of a CRISPR complex with its guide sequence hybridizing to a target sequence results in cleavage of one or both strands in or near the target sequence. A particular guide sequence may be selected by any suitable assay known in the art. In some embodiments, the minimal polyadenylation (mpolyA) signal sequence reported by Xia et al. is provided downstream of a guide sequence but upstream of a Cas sequence. Xia, H. et al., siRNA-Mediated Gene Silencing in Vitro and in Vivo, Nat. Biotechnol., 20:1006-1010 (2002). This allows most of the transcription of the guide sequence from an inducible fusion promoter to terminate at mPolyA, but transcriptional read-through will also produce the Cas. In such embodiments, a full-length polyadenylation or poly(A) signal sequence may be further provided downstream of the Cas gene, with or without a terminator.

In some embodiments, the guide sequence is a guide RNA ("gRNA"). There are two forms of gRNA: one form consists of crRNA and tracRNA, and the other form is sgRNA, which is the two RNAs combined. gRNAs in CRISPR systems specify the target DNAs by Watson-Crick hybridization to a region in the target DNA sequence. The specificity and efficiency of a CRISPR system depend on several factors including nucleotides near the protospacer-adjacent motif (PAM) site and the epigenetic assembly at or near the target site. Moreover, the G-C percentage and secondary structures of the gRNA itself can play an important role in determining efficiency of CRISPR-mediated genome editing. As generally appreciated by those skilled in the art, an approach to screening for an effective editing target site is to test multiple gRNAs to select the optimal gRNA sequence. Exemplary screening methods comprise the steps of incubating cells in the presence of one or more gRNAs from the plurality of gRNAs and identifying gRNAs that disrupt or remove the target gene. It is contemplated that any guide sequence can be inserted into the construct of the inducible CRISPR system of the present invention, such that the encoded guide sequence forms part of a CRISPR complex to selectively silence or otherwise alter the target genome. It is also contemplated that more than one guide sequence can be incorporated in the inducible CRISPR system of the present invention, targeting two distinct sites of a target genome.

A "target sequence" as used herein refers to a sequence to which a guide sequence is designed to have complementarity and often includes a sequence that is unique in the target genome. Full complementarity is not necessarily required, provided there is sufficient complementarity to cause hybridization and to allow formation of a CRISPR complex at the target genome. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. In other embodiments, the target sequence is located in viral or proviral genomes.

As is known, the CRISPR system is applicable to a wide variety of genes in a wide variety of organisms and thus, the disclosed systems, compositions, and methods can be utilized in each of these contexts. Examples of genes which can be targeted by the disclosed systems, compositions, and methods include endogenous genes (i.e., genes that are native to the cell) or genes that are not normally native to the cell. Without limitation these genes include oncogenes, cytokine genes, idiotype (Id) protein genes, prion genes, genes that expresses molecules that induce angiogenesis, genes for adhesion molecules, cell surface receptors, proteins involved in metastasis, proteases, apoptosis genes, cell cycle control genes, genes that express EGF and the EGF receptor, multi-drug resistance genes, such as the MDR1 gene.

In one embodiment, the target sequence of the present invention may specify the amino acid sequence of a host's cellular protein (e.g., a nuclear, cytoplasmic, transmembrane, or membrane-associated protein). In another embodiment, the target sequence of the invention specifies the amino acid sequence of an extracellular protein (e.g., an extracellular matrix protein or secreted protein). As used herein, the phrase "specifies the amino acid sequence" of a protein means that the target sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSF, ETSI, ETV6, FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor-suppressor proteins (e.g., APC, BRCA1, BRCA2, MADH4, MCC, NF 1, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hemicellulases, integrases, inulnases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanlases, recombinases, reverse transcriptases, RUBISCOs, topoisomerases, and xylanases).

In other embodiments, the target sequence of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein that facilitates entry of the pathogen into the host, drug metabolism by the pathogen or host, replication, or integration of the pathogen's genome, establishment or spread of infection in the host, or assembly of the next generation of pathogen. Pathogens include RNA viruses such as flaviviruses, picornaviruses, rhabdoviruses, filoviruses, retroviruses (including lentiviruses) or DNA viruses (such as adenoviruses, poxviruses, herpes viruses, cytomegaloviruses, hepadnaviruses and others). Additional pathogens include bacteria, fungi, helminths, schistosomes and trypanosomes. Other kinds of pathogens can include mammalian transposable elements. Alternatively, the protein may be a tumor-associated protein or an autoimmune disease-associated protein.

In specific embodiments, an inducible CRISPR system of the present invention targets a cellular factor that positively or restrictively regulate HIV-1 replication. In one embodiment, a target sequence is found in the sequence encoding a cellular factor, Cyclin T1. Cyclin T1 is part of Positive Transcription Elongation Factor-b (P-TEFb), which plays a critical role in the regulation of transcription by RNA Polymerase II (Pol II) in Eukaryotes as well as HIV. P-TEFb is a heterodimer of cyclin-dependent kinase 9 (CDK9) and one of the regulatory cyclins (Cyclin T1, T2a, T2b, or K) that bind to and activate CDK9. A P-TEFb kinase-mediated phosphorylation of RNA polymerase II also serves as a master switch to turn on HIV replication. HIV-mediated recruitment and activation of CDK9 specifically requires Cyclin T1, and knocking down either CDK9 or Cyclin T1 has been shown to inhibit HIV transcription. CDK9 can partner with other cyclins and provide redundancy for cellular transcription by P-TEFb thereby mitigating any cytotoxicity. On the other hand, Cyclin T1 is critical for HIV transcription by both TAT-dependent and TAT independent mechanisms. Thus, Cyclin T1 knockdown will disrupt HIV transcription.

As used herein, "nucleic acid construct" or "construct" refers to an isolated polynucleotide that is introduced into a host cell or a segment thereof. A construct may comprise any combination of deoxyribonucleotides, ribonucleotides, and/or modified nucleotides. A construct may be expressed in the cell, or isolated or synthetically produced. The construct may further comprise a promoter, or other sequences that may facilitate manipulation or expression of the construct.

As used herein, "encodes" or "encoding" refers to a DNA and/or RNA sequence that can be processed to generate an RNA and/or polypeptide.

As used herein "operatively linked" or "operatively associated" refers to a functional linkage of at least two sequences. For example, operatively linked includes linkage between a promoter and a second sequence, wherein the promoter sequence initiates and mediates transcription of the second sequence. Operatively associated includes linkage between an inducible element and a promoter, wherein the inducible element acts as a transcriptional activator of the promoter.

The inducible CRISPR system of the present invention further comprises an inducible fusion promoter. "Inducible fusion promoter" refers to a nucleic acid construct that comprises a suitable promoter to drive expression of one or more elements of the CRISPR system and that is operatively associated with an inducible element that is responsive to an inducer. As used herein, "promoter" refers to a region of a construct that is involved in the recognition and binding of an RNA polymerase and other proteins to initiate transcription. The inducible fusion promoter according to the present invention is capable of driving expression of both the Cas and guide sequences of the CRISPR systems. In a preferred embodiment, the inducible fusion promoter comprises a Pol II promoter as a promoter. In some embodiments, the Pol II promoter is operatively associated with HIV-1 LTR. The HIV-1 LTR that is operatively associated with a Pol II promoter preferably comprises the U3R region up to and including the trans-activation response (TAR) element (SEQ ID NO: 11). More preferably, the U5 region that is normally present in a full-length HIV-1 LTR is not included. Furthermore, any Pol II promoter may be used in accordance with the present invention. In one embodiment, the Pol II promoter is a heat shock promoter. In another embodiment, the heat shock promoter is a minimal heat shock promoter. In a further embodiment, the minimal heat shock promoter is the minimal Drosophila hsp70 promoter (SEQ ID NO: 12). Preferably, the minimal Drosophila hsp70 promoter is cloned downstream of the HIV-1 LTR containing TAR as disclosed in the following references that are incorporated herein by reference: U.S. Pat. No. 8,138,327; Unwalla H J, Novel Pol II Fusion Promoter Directs Human Immunodeficiency Virus Type 1-Inducible Coexpression of a Short Hairpin RNA and Protein. J Virol., 80(4):1863-73 (2006); Unwalla H J, Negative Feedback Inhibition of HIV-1 by TAT-Inducible Expression of siRNA. Nat Biotechnol., 22(12):1573-8 (2004).

The inducible CRISPR system of the present invention further comprises an inducible element. As used herein, an "inducible element" includes an element that confers regulation on transcription of a downstream expressed region under inducing conditions. It may be obtained from enhancer regions that are also inducible. Removal of an inducible element would be expected to decrease expression of a downstream region under inducing conditions. Inducible elements (e.g., consensus sequences known in the art) are usually between about 4 and 100 nucleotides in length. In some embodiments, the inducible element is responsive to a viral specific transcription factor. In a further embodiment, the virus is HIV. In a preferred embodiment, the inducible element is HIV-1 TAR (trans-activation response) typically residing within the R region of the HIV-1 LTR, which is believed to be between −17 and +54 with respect to the initiation site of viral transcription. It is believed that the RNA encoded between +1 and +59 has the potential to from an extensive stem-loop secondary structure which, as a portion of the untranslated leader RNA, would be common to all HIV-1 mRNAs. Without being bound by a theory, it is believed that the sequence $^{+30}$CUGGG$^{+34}$ in TAR within the loop of the hairpin structure is required for TAT transactivation. In a specific embodiment, HIV-1 LTR containing the TAR sequences (SEQ ID NO: 11) and a Pol II promoter are operatively associated with one another, with the Pol II promoter being immediately downstream of HIV-1 LTR. More preferably, the Pol II promoter is the minimal Drosophila hsp70 promoter as described above.

In other embodiments, the inducible fusion promoter of the present invention can comprise a drug-inducible promoter (such as tetracycline inducible promoters) as an inducible element to control expression of CRISPR elements in a drug-inducible manner. In a further embodiment, the inducible element can be a promoter sequence of any tissue specific or cell-type specific promoter to control expression of CRISPR systems to alter their tissue- and cell-type expression profiles. For example, a FoxJ1 promoter as an inducible element allows expression only in ciliated cells. For expression in response to transforming growth factor beta (TGF-β), which is often overexpressed in airway diseases, any promoter operatively associated with SMAD-binding elements can induce expression only in the presence of TGF-β. As another example, inducible expression of CRISPR systems in astrocytes can be achieved by the Glial fibrillary acidic protein (GFAP) promoter as an inducible element. Expression of CRISPR systems may also be induced in a cancer-specific manner, for example, by utilizing cancer-specific promoters including those disclosed in Chen X. et al., Cancer-Specific Promoters for Expression-Targeted Gene Therapy: Ran, Brms1 and Mcm5, J. Gene Med., 18(7):89-101 (2016).

As used herein, "inducer" includes an agent that induces, especially a substance that is capable of activating transcription from specific genes within a cell. In some embodiments, the inducer is a tissue specific transcription factor, a viral specific transcription factor, a cellular specific transcription factor, or an engineered transcription factor. In other embodiments, an inducer is a drug such as tetracycline. In one embodiment, the inducer is HIV-1 TAT (trans-activator of transcription) protein, a regulatory protein encoded by the TAT gene in HIV-1. HIV-1 TAT is a 14 kDa viral protein involved in the regulation of HIV-1 transcriptional elongation, and in its presence, viral replication increases by greater than 100-fold. It functions to trigger efficient RNA chain elongation by binding to TAR RNA, which forms the initial portion of the HIV-1 transcript. The interaction between HIV-1 TAT and TAR is critical for virus replication, and mutations in HIV-1 TAT altering the RNA-binding site have been shown to result in defective viruses. Furthermore, viral replication can be strongly inhibited by the overexpression of TAR RNA sequences that act as competitive inhibitors of regulatory protein binding.

In a specific embodiment of the invention, the inducible CRISPR system comprises an HIV-inducible fusion promoter to drive expression of both Cas and guide sequences. In further embodiments, the inducible fusion promoter comprises the minimal Drosophila hsp70 promoter that is operatively associated with HIV-1 LTR containing TAR. Preferably, the guide sequence is placed immediately downstream of the inducible fusion promoter such that transcription of the guide sequence begins from +1 of the minimal Drosophila hsp70 promoter in the presence of an inducer (e.g., HIV-1 TAT) and terminates at the mPolyA reported in Xia, H. et al., siRNA-Mediated Gene Silencing in Vitro and in Vivo, Nat. Biotechnol., 20:1006-1010 (2002). In further embodiments, a Cas sequence is provided downstream of the mPolyA sequence such that transcriptional read-through of the mPolyA occurs to also produce the Cas protein. A full-length polyadenylation or poly(A) signal sequence may be further provided downstream of the Cas gene. A translation initiation site may be further provided upstream of Cas in order to facilitate translation of Cas transcripts.

In an embodiment of the present invention where the target sequence is Cyclin T1 and the inducer is HIV-1 TAT, it is thought that P-TEFb kinase is recruited to an inducible fusion promoter in the presence of HIV-1 TAT and induces transcription of Cas and guide sequences targeting Cyclin T1. Because Cyclin T1 is critical for HIV transcription by both TAT-dependent and TAT independent mechanisms, Cyclin T1 knockdown will disable all HIV transcription for the life of the cell thereby suppressing HIV replication and effecting a functional "cure." Moreover, Cyclin T1 knockdown also ceases transcription from the inducible fusion promoter of the CRISPR system, as its expression is also dependent on the interaction between HIV-1 TAT and Cyclin T1.

FIG. 2A provides an illustration of such self-limiting CRISPR system embodiment (in pLentiCRISPR v2 plasmid (GenScript Biotechnology)). In the presence of HIV-1 TAT (labeled as "Tat"), transcription of both Cyclin T1 gRNA and Cas9 genes is induced from a Pol II promoter, i.e., the minimal *Drosophila* hsp70 promoter (labeled "mhsp 70 Prm") that is operatively associated with HIV-1 LTR up to and including the TAR loop (labeled as ("HIV U3R")). Most of the transcription from the minimal *Drosophila* hsp70 promoter will terminate at the minimal polyA (labeled "Min PolyA") to express the gRNA while transcriptional readthrough will produce the Cas9 (gene labeled "Cas 9"). The strong eukaryotic translation initiation signal CCACC ensures that the first ATG after this sequence is used to initiate translation of the Cas9 gene. A full-length polyadenylation signal sequence (labeled "BGH poly A") is also provided downstream of the Cas9 gene. The co-expression of Cyclin T1 gRNA and Cas9 results in the formation of a CRISPR complex to suppress Cyclin T1, which in turn blocks HIV transcription. Given the critical importance of TAT-Cyclin T1 interaction for HIV transcription, inactivation of Cyclin T1 will irreversibly block all transcription from HIV locking it in a transcriptionally inactive state. Furthermore, since the co-expression of Cyclin T1 gRNA and Cas9 also requires TAT-Cyclin T1 interaction, once Cyclin T1 is knocked down, transcription from the inducible fusion promoter will also be inhibited.

In another aspect of the invention, an inducible CRISPR system further comprises a catalyzing RNA that catalyzes RNA-processing reactions. Without being bound by a theory, one of the limitations of a CRISPR system is believed to be a seemingly paradoxical situation where the guide sequence needs to be retained in the nucleus while the Cas mRNA has to be exported to the cytoplasm for translation. Generally, mRNA processing of Pol II-based transcripts results in addition of the 5'-methyl guanosine cap (5' cap) to all mRNAs. Thus, Pol II-based transcripts of the guide sequence and Cas have the 5' cap. The 5' cap facilitates nuclear export and translation of the mRNAs containing it, while nuclear retention of mRNA requires the removal of the 5' cap. If the 5' cap remains on the majority of the guide sequence transcripts, they would be exported from the nucleus to the cytoplasm thereby decreasing CRISPR efficacy.

To overcome this limitation, some embodiments of an inducible CRISPR system of the present invention include a sequence encoding a catalyzing RNA in their construct to remove the 5' cap from the guide sequence transcripts. In some embodiments, the catalyzing RNA is a ribozyme, such as the hammerhead ribozyme, the hairpin ribozyme, the VS ribozyme, or the Leadzyme. In some embodiments, a ribozyme is incorporated into the inducible CRISPR system immediately upstream of a guide sequence. In further embodiments, a second ribozyme is inserted downstream of the guide sequence but before mPolyA. In other embodiments, ribozymes can be placed between two or more contiguous gRNAs targeting two distinct sites of the target genome, for example, HIV proviral DNA, to prevent viral escape. Preferably, ribozyme is a cis-cleaving ribozyme. More preferably, the ribozyme is modified such that it has lower cleavage efficiency than its unmodified counterpart. In one embodiment, the modified cis-cleaving ribozyme is a minizyme. Minizymes are variants of hammerhead ribozymes in which the stem-loop II sequence has been replaced by a shorter linker sequence. See Persson T. et al., Selection of Hammerhead Ribozyme Variants with Low Mg2+ Requirement: Importance of Stem-Loop II. Chembiochem., 3(11):1066-71 (2002); see also FIG. 3B. Minizymes demonstrate slightly lower RNA cleavage efficiency compared to full-length hammerhead ribozymes. Hammerhead ribozymes can cleave any RNA as long as the ribozyme arms can hybridize with the target RNA, and the target contains an NUX triplet where N=A, G, C, or U, and X=A, U or C for optimal cleavage. The minizyme incorporated in the LTRhsp-MzgRNA-mpolyA-Cas9pA construct (FIG. 3B, top) recognizes a canonical GUC cleavage site while the weaker minizyme incorporated in LTRhsp-Mz$_{wk}$gRNA-mpolyA-Cas9pA (FIG. 3B, bottom) recognizes a weaker non-canonical GUG cleavage site. The lower activity of minizymes mediates cap removal and nuclear retention of a proportion of the Pol II-based transcripts including the transcripts for guide sequences (see FIG. 3A), while the uncleaved transcripts with their intact 5' cap would be exported to the cytoplasm. Minizymes have been demonstrated to affect HIV inhibition, but ribozymes have never been reported to be used in a CRISPR system or for its expression.

In another aspect of the invention, a cell containing an inducible CRISPR system of the present invention is provided. By "host cell" it is meant a cell that contains an introduced nucleic acid construct and supports the replication and/or expression of the construct. In one embodiment, the host cell is a cell that naturally contains the inducer. In other embodiments, the host cell is provided with an inducer by an external source. In another embodiment, the host cell is one that is infected by a virus or bacteria and thus produces an inducer. In one embodiment, the host cell is one that is infected by HIV-1, and thus produces TAT. In one embodiment, host cells infected with HIV-1 can efficiently induce expression of the CRISPR system according to the present invention. In a further embodiment, the cell is one that is transfected with a nucleic acid construct comprising a HIV-1 TAT-coding sequence operatively linked to a promoter, such that HIV-1 TAT is produced in the cell. The promoter associated with the TAT-encoding nucleic acid sequence may be any promoter, such as a constitutive promoter, a tissue-preferred promoter, an inducible fusion promoter, or a de-repressible promoter.

The tem). "introducing" encompasses a variety of methods of introducing nucleic acids into a cell, either in vitro or in vivo, such methods including transformation, transduction, transfection, and infection. Vectors are useful and preferred agents for introducing nucleic acids encoding the CRISPR complex into cells. As used herein, "vector" includes reference to nucleic acids used to introduce a polynucleotide of the invention into a host cell. Possible vectors include but are not limited to plasmid vectors, viral vectors, and expression vectors. A plasmid is a circular double stranded DNA loop into which additional DNA segments can be inserted, such as by standard molecular cloning techniques. Viral vectors include virally derived DNA or RNA sequences for packaging into a virus and can be retroviral vectors, lentiviral vectors, or other vectors such as adenoviral vectors or adeno-associated vectors. Expression vectors permit transcription of a nucleic acid inserted therein and include one or more elements that may facilitate manipulation of the vector and/or operatively linked to the nucleic acid sequence to be expressed. Examples of such elements include, but are not limited to, the cytomegalovirus (CMV) promoter, CMV enhancer, SV40 promoter, SV40 enhancer, the Woodchuck hepatitis virus post-transcriptional regulatory element (WPRE), a central polypurine tract (cPPT). See also FIG. 2A.

In a further aspect of the invention, a method for silencing or otherwise editing a target genome is provided. The method employs the inducible CRISPR system described above, in which a guide sequence such as gRNA is designed to a target sequence and inserted into a construct of the inducible CRISPR system. Upon introduction into a cell and upon induction of the inducible CRISPR system in the presence of an inducer, the guide sequence, along with at least one Cas protein, is produced from the CRISPR system. The guide sequence hybridizes to the target sequence so as to guide the associated Cas protein to the target genome for gene editing. In one embodiment, the cell is one that is infected with HIV-1, thereby producing an inducer unique to HIV-1 such as HIV-1 TAT. Induced expression of a CRISPR complex targeting a cellular factor that regulates HIV-1 replication results in inhibition of viral replication, thus establishing a negative feedback loop. In another embodiment, the cell is one that is transfected with a nucleic acid construct comprising a nucleic acid sequence encoding HIV-1 TAT, and the invention provides a method of inhibiting any target sequence. In some embodiments, single introduction of the CRISPR system into target cells leads to sustained suppression of HIV replication.

Transformation protocols as well as protocols for introducing nucleotide sequences into cells may vary depending on the type of cell targeted for transformation. Suitable methods of introducing a construct into cells are well known in the art and include microinjection, electroporation, direct gene transfer, ballistic particle transformation, viral transformation, retroviral transformation, and the like. In some embodiments, transient expression may be desired. In those cases, standard transient transformation techniques may be used. Such methods include, but are not limited to viral transformation methods, and microinjection of DNA or RNA, as well other methods well known in the art.

Initial identification and selection of cells and/or plants comprising the DNA constructs may be facilitated by the use of marker genes. Gene targeting can be performed without selection if there is a sensitive method for identifying recombinants, for example if the targeted gene modification can be easily detected by PCR analysis, or if it results in a certain phenotype. Typically, however, identification of gene targeting events will be facilitated by the use of markers. Useful markers include positive and negative selectable markers as well as markers that facilitate screening, such as visual markers.

In another aspect, the inducible CRISPR system of the present invention is formulated as a pharmaceutical composition that comprises a pharmacologically effective amount of an inducible CRISPR system. The phrases "pharmacologically effective amount" and "therapeutically effective amount" or simply "effective amount" refer to that amount of the inducible CRISPR system effective to produce the intended pharmacological, therapeutic or preventive result. For example, if a given clinical treatment is considered effective when there is at least a 20% reduction in a measurable parameter associated with a disease or disorder, a therapeutically effective amount of an inducible CRISPR system for the treatment of that disease or disorder is the amount necessary to affect at least a 20% reduction in that parameter.

Pharmaceutical composition comprising the inducible CRISPR system can be administered to a subject once daily. However, the therapeutic agent may also be dosed in dosage units containing two, three, four, five, six or more sub-doses administered at appropriate intervals throughout the day. In that case, the inducible CRISPR system contained in each sub-dose may be correspondingly smaller in order to achieve the total daily dosage unit. Regardless of the formulation, the pharmaceutical composition must contain the inducible CRISPR system in a quantity sufficient to suppress or alter the expression of the target gene in the subject being treated. The composition can be compounded in such a way that the sum of the multiple units of the inducible CRISPR system together contain a sufficient dose.

In a further embodiment, the pharmaceutical composition according to the present invention further comprises a pharmaceutically acceptable carrier well known to a person skilled in the art. The carrier can generally be any suitable medium by which the desired purpose is achieved, provided that it does not affect the CRISPR system's capability to be directed to the desired target and to achieve the desired effect. Particularly, the carrier should not deteriorate the pharmacological potency of the active ingredient and the capability of the complex to be directed to a desired target within, or on, the animal body. Exemplary carriers include water, saline, buffered saline, other physiologically acceptable aqueous solutions containing salts and/or buffers, dextrose, glycerol, ethanol, and combinations thereof. Further examples include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter. The pharmaceutically acceptable carrier may also be micellar structures, such as a liposomes, capsids, capsoids, polymeric nanocapsules, or polymeric microcapsules. The pharmaceutical composition according the present invention may further comprise conventional ingredients in conventional proportions, with or without additional active ingredients.

Depending on the form of the pharmaceutical composition and/or mode of administration of the present invention, pharmaceutically acceptable carriers may include, but are not limited to, pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid, or talc. If desired and suitable, a coating material may also be used such as glyceryl monostearate or glyceryl distearate, for example, to delay absorption in the gastrointestinal tract if the pharmaceutical composition is in the form of a solid form.

In one embodiment, the pharmaceutical composition according to the present invention is in the form of solids including tablets, filled capsules, powder and pellet forms. In another embodiment, the pharmaceutical composition may be in the powder form, in which the pharmaceutically accepted carrier is a finely divided solid that is in a mixture with the finely divided active ingredient. In a further embodiment, the pharmaceutical composition according to the present invention is a sustained release system such as semipermeable matrices of solid hydrophobic polymers containing the inducible CRISPR system of the present invention. In another embodiment, the pharmaceutical composition is in a liquid form such as aqueous or non-aqueous solutions, suspensions, emulsions, elixirs, and capsules filled with the same.

The pharmaceutical composition according to the present invention can be administered through, for example, oral, rectal, bronchial, nasal, topical, buccal, sub-lingual, transdermal, vaginal, intramuscular, intraperitoneal, intravenous, intra-arterial, subcutaneous, intracerebral, intraocular administration or in a form suitable for administration by inhalation or insufflation, including powders and liquid aerosol administration, or intraparenteral infusion. Administration may be also by way of other carriers or vehicles such as patches, micelles, liposomes, vesicles, implants (e.g., microimplants), synthetic polymers, microspheres, nanoparticles, and the like.

In one embodiment, the pharmaceutical composition may be formulated for parenteral administration (e.g., by injection, for example bolus injection or continuous infusion). In addition, the composition may be presented in unit dose form in ampoules, pre-filled syringes, and small volume infusion or in multi-dose containers with or without an added preservative. The composition may be in forms of suspensions, solutions, or emulsions in oily or aqueous vehicles. The composition may further contain formulation agents such as suspending, stabilizing and/or dispersing agents. In a further embodiment, the active ingredient of the composition according to the invention may be in a powder form, obtained by aseptic isolation of sterile solid or by lyophilization from solution for constitution with a suitable vehicle, e.g., sterile, pyrogen-free water, before use.

In one embodiment, the composition may be formulated in aqueous solutions for oral administration. The composition may be dissolved in suitable solutions with added suitable colorants, flavors, stabilizing and thickening agents, artificial and natural sweeteners, and the like. In addition, the composition may further be dissolved in solution containing viscous material, such as natural or synthetic gums, resins, methylcellulose, sodium carboxymethylcellulose, or other well-known suspending agents.

In one embodiment, the composition is applied topically or systemically or via a combination of both. The composition may be formulated in the forms of lotion, cream, gel, and the like.

In one embodiment, the composition can be applied directly to the nasal cavity by conventional means, for example with a dropper, pipette, or spray. The compositions may be provided in single or multi-dose form. Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin.

Furthermore, the composition may be provided in the form of a dry powder in a suitable powder base such as lactose, starch, starch derivatives such as hydroxypropylmethyl cellulose and polyvinylpyrrolidone (PVP). Conveniently, the powder carrier will form a gel in the nasal cavity. The powder composition may be presented in unit dose form for example in capsules or cartridges of, e.g., gelatin, or blister packs from which the powder may be administered by means of an inhaler.

In one embodiment, the pharmaceutical composition is provided in unit dosage forms, wherein the composition in desired form is divided into unit doses containing appropriate quantities of the active ingredient. The unit dosage form can be a packaged preparation, the package containing discrete quantities such as packaged tablets, capsules, and powders in vials or ampoules. Moreover, the unit dosage form can be a capsule, tablet, cachet, or lozenge itself, or it can be the appropriate number of any of these in packaged form. In some embodiments, tablet or capsule forms are for oral administration and liquid form are for intravenous administration and continuous infusion.

In a further aspect, the present invention relates to a method for treating a subject having a disease or at risk of developing a disease caused by the expression of a target gene. The inducible CRISPR system according to the present invention can act as a novel therapeutic agent for controlling one or more of cellular proliferative and/or differentiative disorders, disorders associated with bone metabolism, immune disorders, hematopoietic disorders, cardiovascular disorders, liver disorders, viral diseases, or metabolic disorders. Non-limiting examples of target diseases include cancer, Sickle Cell disease, HIV/AIDS, Beta-Thalassemia, and ophthalmic diseases such as Leber Congenital Amaurosis (LCA)-causing Splice Defect. In the treatment of disease, the method comprises administering a pharmaceutical composition comprising the inducible CRISPR system to the patient (e.g., human) and inducing the inducible CRISPR system in or around the cells or tissue exhibiting the disease, such that expression of the target genes of diseased cells and/or tissues is specifically silenced or otherwise altered. In the prevention of disease, the target gene may be one which is required for initiation or maintenance of the disease, or which has been identified as being associated with a higher risk of contracting the disease. Alternatively, the inducible CRISPR system according to the present invention may be utilized in ex-vivo or cellular gene therapy in a manner known to those skilled in the art. For example, the inducible CRISPR system can be used to knock out a mutated gene or introduce a functional replacement gene in select cells that have been removed from a patient. The modified cells may be expanded in culture and returned to the patient.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, cats; live stocks such as horses, cattle, pigs, sheep, goats, and chickens; and other animals such as mice, rats, guinea pigs, and hamsters.

Further examples of cellular proliferative and/or differentiative disorders that may be treated with the inducible CRISPR system of the present invention include cancer, e.g., carcinoma, sarcoma, metastatic disorders, or hematopoietic neoplastic disorders, e.g., leukemia. A metastatic tumor can arise from a multitude of primary tumor types, including but not limited to those of prostate, colon, lung, breast, and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplatic cells of hematopoictic origin, e.g., arising from myeloid, lymphoid or erythroid lineages, or precursor cells thereof.

The present invention can also be used to treat a variety of immune disorders, in particular those associated with overexpression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizinig hemorrhagic encephalopathy, idiopathic bilateral progressive sensorineural hearing, loss, aplastic anemia, pure red cell anemia, idiopathic thrombocytopenia, polychonidritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-lost disease, cases of transplantation, and allergy.

In another embodiment, the invention relates to a method for treating viral diseases, including but not limited to human papilloma virus, hepatitis C, hepatitis B, herpes simplex virus (HSV), HIV-AIDS, poliovirus, and smallpox virus. Inducible CRISPR system of the invention are prepared as described herein to target expressed sequences of a virus, thus ameliorating viral activity and replication. The inducible CRISPR system can be used in the treatment and/or diagnosis of viral infected tissue, both animal and plant. Also, such system can be used in the treatment of virus-associated carcinoma, such as hepatocellular cancer.

In yet another embodiment, the inducible CRISPR system of the present invention can also be used to silence or edit the expression of the multi-drug resistance 1 gene ("MDR1"). "Multi-drug resistance" (MDR) broadly refers to a pattern of resistance to a variety of chemotherapeutic drugs with unrelated chemical structures and different mechanisms of action.

Furthermore, it would be appreciated by those skilled in the art that the methods described in the present invention would not only apply to treatment in a subject, but could be applied to cell cultures, organs, tissues, or individual cells in vivo or in vitro.

The inducible CRISPR system according to the present invention can be used in areas outside of treatment and/or pathological conditions in animals and plants. For example, in some embodiments, the inducible CRISPR system can be induced in plants and plant cells in a targeted manner to disrupt or provide new or enhanced phenotypes. In the food or feed production context, for example, different or higher nutritional contents, oil production, and/or yield increase may prove useful in certain plants including crops such as grains, pulses, tubers, and other vegetables as well as fruits. Further, alterations in genetic expression in livestock, poultry, fish, and edible insects or their cells may also be achieved utilizing the inducible CRISPR system of the present invention. In other embodiments, the inducible CRISPR system can be introduced to plants such as rape and algae for production of resources such as vegetable oils and biofuels including alcohols. The plants may be engineered to express or overexpress high levels of these resources for efficient production. The inducible CRISPR system may be introduced and induced in specific cell or tissue types in vivo, ex vivo or in vitro using the methods described herein as well as known in the art.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" of or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

Materials and Methods

Cyclin-T1 CRISPR gRNAs. Three gRNA sequences targeting Cyclin T1 were obtained from GenScript (www.genscript.com/gRNA-detail/904/CCNT1-CRISPR-guide-RNA.html). These gRNAs differed by their guide regions and were designated as gRNA-1 (AATAGCC-CATCCCGTCGTTT, SEQ ID NO: 13), gRNA-2 (TC-CACGCCAAAACGACGGGA, SEQ ID NO: 14), and gRNA-3 (CCTACCTCACTTCTAGTATC, SEQ ID NO: 15). They were pre-cloned in pLentiCRISPR v2 plasmid (GenScript Biotechnology). The plasmids were identified as pLentiCRISPR-gRNA-1, pLentiCRISPR-gRNA-2, or pLentiCRISPR-gRNA-3, depending on the incorporated guide regions. In these constructs, the gRNAs were expressed from the U6 promoter and Cas9 was expressed from the Pol II EFS promoter with the lentiviral LTR polyA signal sequence serving as transcriptional termination for Cas9.

Cell culture experiments. HeLa-CD4 and HIV-infected HeLa-CD4 cells were obtained from NIH AIDS Reagent Program (Cat #153 and Cat #1301, respectively) and maintained in DMEM with 10% (vol/vol) fetal bovine serum ("FBS"). These cells can be considered as stringent models of HIV replication for testing therapeutics as they have distinct advantages in that most, if not all, cells harbor the provirus and provide microgram quantities of HIV p24 output. The human T-cell line CEM was maintained in RPMI medium 1640 (GibcoBRL) supplemented with 2 mM glutamine, 100 units/ml penicillin, 100 μg/ml streptomycin, and 10% (vol/vol) FBS ("complete growth medium"). For all plasmid transfections in HeLa-CD4 cells (both HIV-infected and uninfected), cells were grown to 60% confluence in 6 well plate, and 1 μg of plasmid DNA was complexed with lipofectamine 2000 in Opti-MEM™ according to manufacturers' protocol (Thermo Fisher Scientific, Cat #51985091). Plasmid transfections in CEM-T cells was done by electroporation using Neon electroporation system and kit (Thermo Fisher Scientific, Cat #MPK1025), using the protocol standardized for CEM cells by the manufacturer (Thermo Fisher Scientific). At designated time points, culture supernatants were collected for HIV p24 viral antigen analysis as an index of HIV infection. The lentiviral backbone plasmid pHIV-7-GFP was transfected as a control for all transfection experiments. See Unwalla H J, Novel Pol II Fusion Promoter Directs Human Immunodeficiency Virus Type 1-Inducible Coexpression of a Short Hairpin RNA and Protein. J Virol., 80(4):1863-73 (2006); Unwalla H J, Negative Feedback Inhibition of HIV-1 by TAT-Inducible Expression of siRNA. Nat Biotechnol., 22(12):1573-8 (2004).

HIV-1 anti-viral assay. Culture supernatant was collected on designated days and HIV p24 viral antigen was measured from cultured supernatants using p24 ELISA kit (ZeptoMetrix Corp. Cat #0801200) according to the manufacturer's protocol.

Cell viability assay. Trypan blue staining was used to determine viability and live cell counts for HeLa-CD4 cells (infected/uninfected) as well as CEM T-cells. For HeLa-CD4 cells, the cells were trypsinized with Trypsin/EDTA (TE) and Trypsin Neutralizing Solution (TNS), and the cells were resuspended in growth medium and 10 μL of suspension was mixed with equal volume of trypan blue and loaded onto counting slides (Bio-Rad, Cat #1450011). The cells were counted within 10 seconds of trypan blue staining by TC20 Automated cell counter (Bio-Rad). For CEM T-Cells, 10 μL of culture suspension was mixed with equal volume of trypan blue and loaded onto counting slides and cells counts were determined using TC20 Automated cell counter within 10 seconds of trypan blue staining.

Infection of CEM-T cells. $3\times10^6$ CEM-T-cells were infected with 100 ngs p24-equivalent of X4-tropic viral strain HIV IIIB and 2 mg/ml polybrene. After 24 hours, cells were centrifuged, and the culture media was replaced with 5 ml of the complete growth medium and allowed to propagate in T-25 culture flask for 12 days. The culture supernatant was collected every 72 hours and analyzed for HIV p24 viral antigen to monitor infection. The culture medium was also replaced every 72 hours. Cells were then divided into aliquots of $10^6$ infected cells in RPMI with 10% (vol/vol) FBS devoid of antibiotics, before electroporation with each CRISPR system construct (or lentiviral vector control). Electroporation was performed with the Neon transfection system (Thermofisher) using protocol standardized by the manufacturer for CEM cells (Voltage: 1230V; Width: 45 millisecs; Pulses: 1 pulse). Following electroporation, cells were resuspended in RPMI with 10% (vol/vol) FBS in 24 well plate. After 0/N incubation the media was replaced with the complete growth medium including antibiotics.

Real-Time qRT-PCR. Total RNA was extracted from the uninfected and HIV-infected HeLa-CD4 cells by post-transfection of plasmids on designated days using the Qiagen RNeasy mini kit (Cat #74104). The complementary DNA (cDNA) was reverse transcribed using the high-capacity cDNA reverse transcription kit (Applied Biosystem, Cat #4368814). This technique was performed on the Bio-Rad CFX96 real-time system using validated TaqMan probes (Life Technologies/Applied Biosystem: HIV1-LTR, Cat #Pa03453409_s1; GAPDH, Cat #Hs02758991_g1). qRT-PCR results are represented as relative quantification normalized against internal control as a GAPDH.

Western Blot Method. Cells were lysed with RIPA (radioimmunoprecipitation assay) buffer (Thermo Fisher Scientific, Cat #89901) with Halt™ Protease Inhibitor Cocktail (Thermo Fisher Scientific, Cat #78429). The protein concentration was determined by the method of Pierce™ BCA Protein Assay Kit (Thermo Fisher Scientific, Cat #23225) in accordance with the manufacturer's instructions. Equal amounts of total protein were loaded onto 4-20% precast polyacrylamide gel (Bio-Rad, Cat #4568094) and run at 100 V. After the protein was separated, it was transferred onto a polyvinylidene difluoride (PVDF) membrane. The transfer blot was thereafter subject to blocking by 10% blocking solution for 1 hour. The blot was then incubated overnight in primary antibodies for CRISPR-Cas9 (1:1000; Thermo Fisher Scientific, Cat #MA1-202), Cyclin T1 (1:1000; Cell Signaling, Cat #81464), and α-tubulin (1:1000; Cell Signaling, Cat #2125), with 5% blocking solution. After incubation, the blot was washed with TBS-T and further incubated for 1 hour with horseradish-peroxidase-conjugated anti-rabbit secondary antibody, which was diluted 1:2500 with 1% blocking solution. The blotted protein bands were detected in ChemiDoc (Bio-Rad) using SuperSignal West Femto Maximum Sensitivity Substrate (Thermo Fisher Scientific, Cat #34095), following the kit manufacturer's recommendations. The blotted protein was quantified using the Quantity One software system (Bio-Rad) and values were normalized to α-tubulin.

Statistical analysis. Unless otherwise stated, data were expressed as mean±SEM from at least 3 different experiments. The data were subjected to statistical analysis using unpaired t-tests or ANOVA followed by Tukey Kramer's honestly significant difference test for multiple comparisons as appropriate. The significance was considered at the level of $p<0.05$.

EXAMPLES

Following are Examples which are offered by way of illustration and are not intended to limit the invention. Various modifications or changes in light thereof will be suggested to persons skilled in the art and are to be included within the spirit and purview of this application. Unless otherwise stated, these Examples utilized the methods, techniques, and materials as described in Materials and Methods above.

Example 1: Screening for an Optimal gRNA Target Site

Three different gRNA sequences—gRNA-1, gRNA-2 and gRNA-3 were screened to determine an optimal target site for Cyclin T1 in terms of their ability to knock down Cyclin T1 protein, suppress HIV p24, and maintain cell viability. In each of these experiments, lentiviral vector backbone pHIV-7-GFP was used as a control and as an index of transfection efficiency. The three gRNAs were purchased as lentiviral vector clones from GenScript, and identified as "pLentiCRISPR-gRNA-1," "pLentiCRISPR-gRNA-2," and "pLentiCRISPR-gRNA-3." In these constructs, the U6 promoter drives Pol III-mediated and constitutive gRNA expression and a Pol II EFS promoter drives constitutive Cas9 expression.

For their ability to knock down Cyclin T1, the three gRNA vector clones were tested individually in transient transfection assays in HeLa-CD4 cells. 8 days post-transfection, Cyclin T1 protein levels were analyzed by western blot analyses, normalized to α-tubulin. In order to determine the extent of correlation between Cyclin T1 knockdown by the three gRNAs and HIV inhibition, chronically infected models of HeLa-CD4 cells were used. The HIV-infected HeLa-CD4 cells were transfected individually with pLentiCRISPR-gRNA-1, pLentiCRISPR-gRNA-2 or pLentiCRISPR-gRNA-3. Individual culture supernatants were analyzed on days 6 and 8 post-transfection by enzyme-linked immunosorbent assay (ELISA) for HIV p24, which is an indicator of HIV infection. Experiments were terminated on day 8, and the cells were trypsinized, followed by the treatment with a trypsin neutralization buffer. The cells were then washed to remove trypsin and resuspended in DMEM with 10% vol/vol FBS for analysis. The total number of live cells and percent viability for each assay were determined by trypan blue staining. Transfection of all HeLa-CD4 cells was conducted using lipofectamine 2000 as a transfection reagent.

Figure 1A:
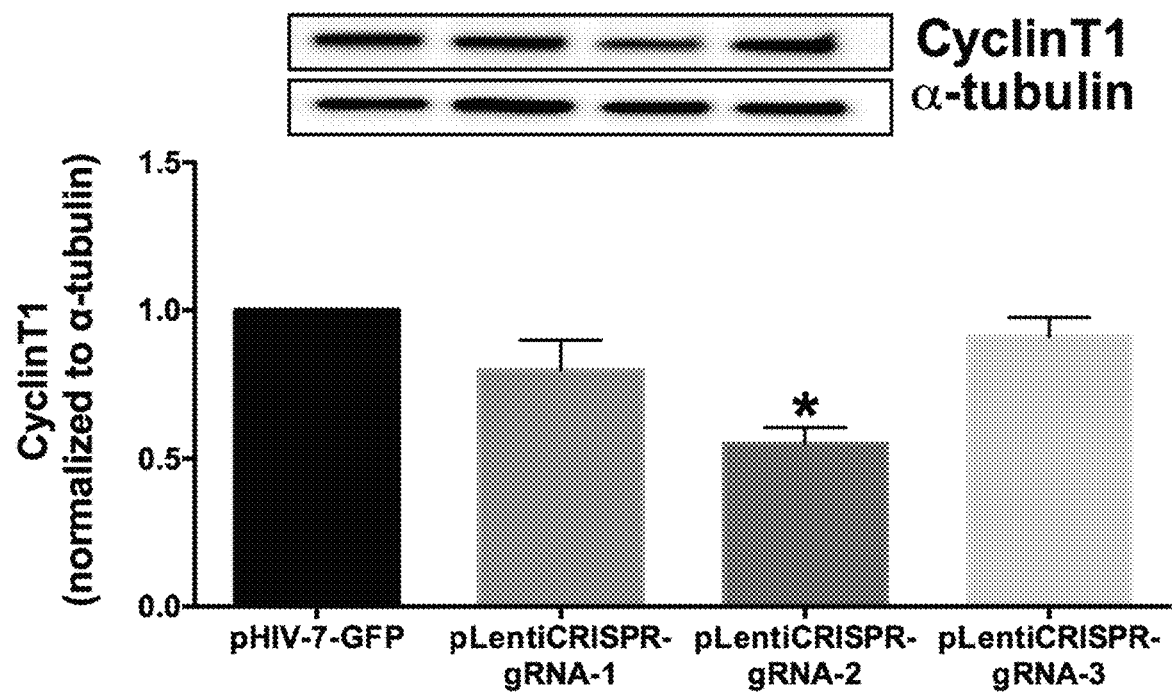
FIG. 1A shows results of Western blot analysis normalized to α-tubulin and a graph comparing Cyclin T1 levels in HeLa-CD4 cells transfected with lentiviral vector clones, each incorporating one of three different gRNA sequences targeting Cyclin T1: gRNA-1, gRNA-2, and gRNA-3. Results show that 8 days after transfection, gRNA-2 exhibited maximal suppression of Cyclin T1. n=mean+/−SEM from 3 independent experiments. *=significant from control.
Figure 1B:
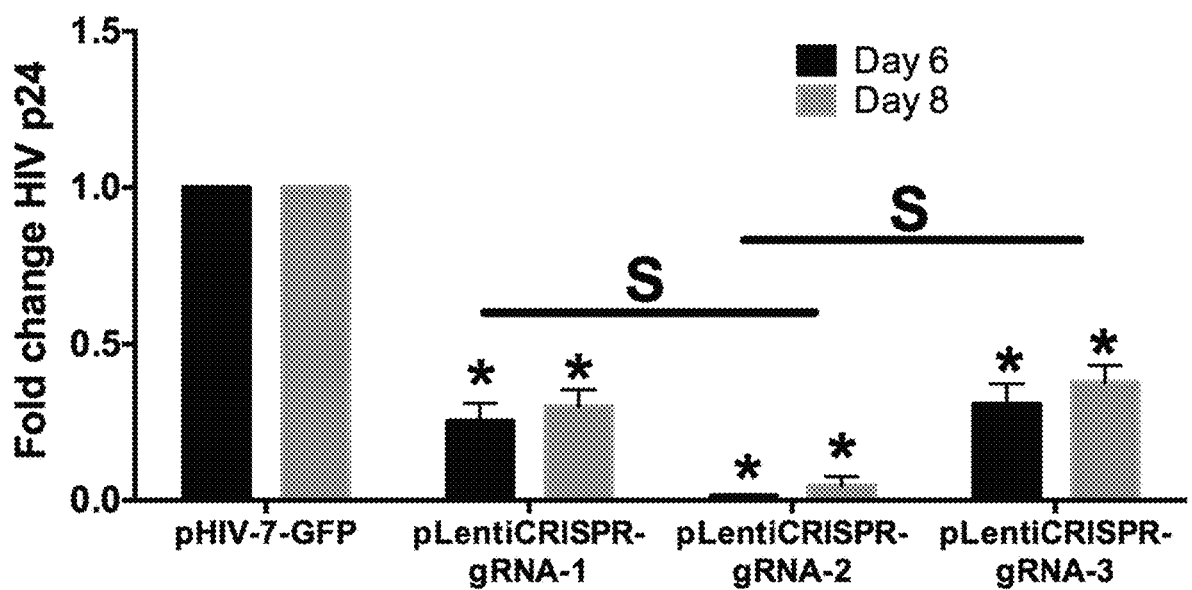
FIG. 1B shows a graph comparing fold changes in HIV p24 levels in HIV-infected HeLa-CD4 cells transfected with lentiviral vectors, each incorporating gRNA-1, gRNA-2, or gRNA-3. On days 6 and 8 post-transfection, all three gRNAs exhibited suppression of HIV p24 levels, while gRNA-2 achieving the most suppression. n=mean+/−SEM from 3 independent experiments. *=significant from control. S=significant from each other (p<0.05).
Figure 1C:
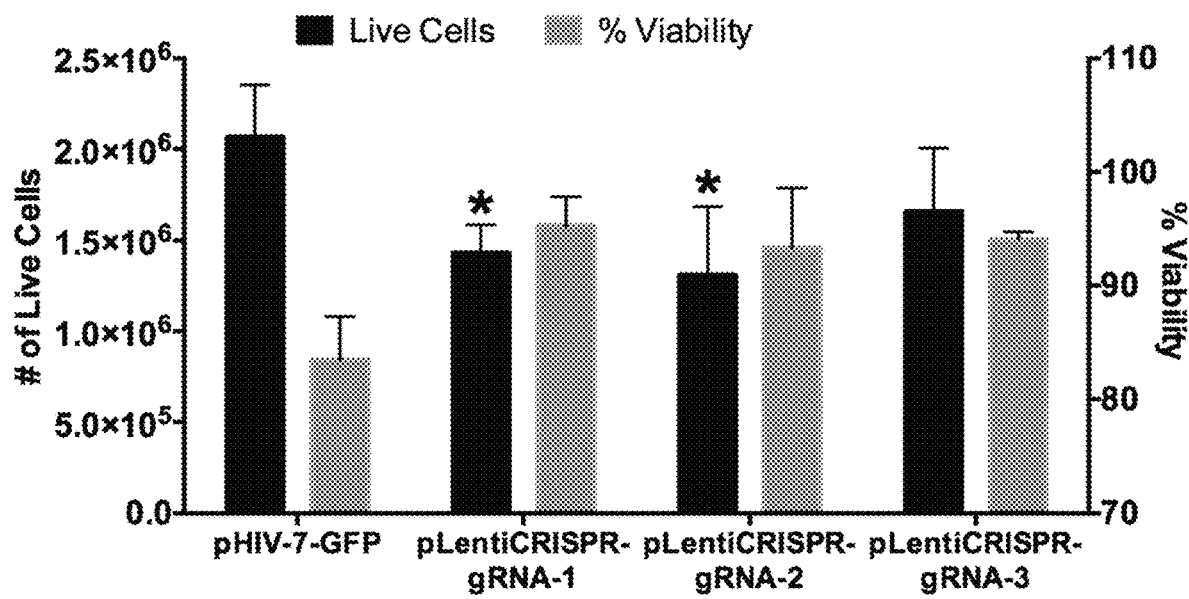
FIG. 1C shows a graph comparing the number of live cells and cell viability 8 days after transfection with lentiviral vector clones each incorporating gRNA-1, gRNA-2, or gRNA-3. The results demonstrate that Cyclin T1 knockdown in HIV-infected HeLa-CD4 cells did not adversely affect cell viability and live cell counts compared to control. n=mean+/−SEM from 3 independent experiments. *=significant from control.

As shown in FIG. 1A through 1C, pLentiCRISPR-gRNA-2 showed the best overall outcome while all three gRNAs demonstrated HIV suppression. LentiCRISPR-gRNA-2 demonstrated maximal suppression of Cyclin T1 8 days post-transfection (FIG. 1A) and of HIV p24 at both 6 and 8 days post-transfection (FIG. 1B). While a small viral rebound was observed on day 8 as opposed to about 98% suppression of HIV on day 6 post-transfection with p-LentiCRISPR-gRNA-2, this is possibly from untransfected cells in the culture population. In any event, the p24 suppression level on day 8 achieved by p-LentiCRISPR-gRNA-2 is statistically significant from other gRNAs. Given that the transfected plasmid would be eliminated from the cultures by dilution by day 8, and that HIV suppression was still observed 8 days following transfection with all three gRNAs, the results suggest that Cyclin T1 inactivation by a single delivery of CRISPR constructs is sufficient to mediate prolonged suppression. Furthermore, FIG. 1C shows that Cyclin T1 suppression in HIV-infected HeLa-CD4 cells does not adversely affect overall cell viability and live cell counts compared to control, although there was a statistically significant decline in the number of live cells in all gRNA vector clones, including pLentiCRISPR-gRNA-2.

Example 2: Construction of HIV-Inducible CRISPR System Constructs

HIV LTR-Minimal *Drosophila* Hsp70 Fusion Promoter

In one embodiment, an inducible CRISPR system of the present invention comprises the HIV LTR-minimal *Drosophila* hsp70 fusion promoter which was disclosed in: U.S. Pat. No. 8,138,327; Unwalla H J, Novel Pol II Fusion Promoter Directs Human Immunodeficiency Virus Type 1-Inducible Coexpression of a Short Hairpin RNA and Protein. J Virol., 80(4):1863-73 (2006); Unwalla H J, Negative Feedback Inhibition of HIV-1 by TAT-Inducible Expression of siRNA. Nat Biotechnol., 22(12):1573-8 (2004), all of which are incorporated herein by reference. To prepare this fusion promoter, the ecdysone and glucocorticoid response elements upstream of the minimal *Drosophila* hsp70 promoter component were removed from the pIND vector (Invitrogen) and replaced with the HIV-1 LTR up to and including the TAR element. The HIV LTR-minimal *Drosophila* hsp70 fusion promoter used in this Example was PCR-amplified using the 5' primer complementary to the TAR loop and containing a KpnI site GGTACC (SEQ ID NO: 1) and the 3'primer (SEQ ID NO: 2), from the LTRhsp-shRNA plasmid previously reported in Unwalla H J, Negative Feedback Inhibition of HIV-1 by TAT-Inducible Expression of siRNA. Nat Biotechnol., 22(12):1573-8 (2004).

LTRhsp-gRNA-mpolyA

The gRNA-2 sequence (comprising the guide and scaffold regions) was PCR amplified using flanking primers based on the sequence provided by GenScript (SEQ ID NO. 3 and SEQ ID NO: 4). The PCR products of HIV LTR-minimal *Drosophila* hsp70 fusion promoter and gRNA-2 were kinased and blunt-end ligated to each other. The ligated product was PCR-amplified using the 5' primer of SEQ ID NO: 1 and the 3' primer of SEQ ID NO: 4 to obtain the LTRhsp-gRNA fragment. The minimal polyadenylation (mpolyA) signal sequence was likewise PCR-amplified from the LTRhsp-shRNA plasmid described above using the primers flanking the mpolyA (SEQ ID NO: 5 and SEQ ID NO: 6). The mpolyA PCR product was kinased and ligated to the LTRhsp-gRNA fragment. This ligated product was reamplified using the 5' primer of SEQ ID NO: 1 and a 3' primer of SEQ ID NO: 6 (with XbaI site TCTAGA), to obtain the LTRhsp-gRNA-mpolyA fragment.

LTRhsp-gRNA-mpolyA-Cas9pA

The resulting PCR product of LTRhsp-gRNA-mpolyA fragment with KpnI and XbaI terminal sites was digested with KpnI and XbaI and ligated in a similarly digested pLentiCRISPR-gRNA-2 which had been pre-cloned in pLentiCRISPR v2 plasmid (GenScript Biotechnology). In pLentiCRISPR-gRNA-2, the U6 promoter drives gRNA-2 expression and a Pol II EFS promoter drives Cas9 expression. Ligation resulted in substitution of the U6-gRNA region and the EFS promoter upstream of Cas9 in pLentiCRISPR-gRNA-2 with the LTRhsp-gRNA-mpolyA to obtain LTRhsp-gRNA-mpolyA-Cas9 pA (SEQ ID NO: 18). In this new construct, a strong eukaryotic translation initiation site CCACC served as a Kozak sequence immediately upstream of Cas9 and ensured appropriate Cas9 translation initiation.

NF-κβ and SP1 Deletion Mutants

The NF-κβ or SP1 deletion mutants of LTRhsp-gRNA-mpolyA-Cas9pA construct, which are identified as LTR (ΔNF-κβ)-gRNA-mpolyA-Cas9pA and LTR(ΔSP1)-gRNA-mpolyA-Cas9 pA, were generated by PCR-based deletion of the NF-κβ or SP1 sites in the HIV-1 LTR using LTRhsp-gRNA-mpolyA-Cas9pA as a template.

Ribozyme-Embedded LTRhsp-gRNA-mpolyA-Cas9pA Constructs

Two types of ribozyme-embedded LTRhsp-gRNA-mpolyA-Cas9pA constructs were prepared, LTRhsp-MzgRNA-mpolyA-Cas9pA (SEQ ID NO: 19) and LTRhsp-Mz$_{wk}$gRNA-mpolyA-Cas9pA. "Mz" indicates a minizyme that recognizes a canonical GUC cleavage site (SEQ ID NO: 20), while "Mz$_{wk}$" indicates a "weaker" minizyme that recognizes a non-canonical GUG cleavage site (see SEQ ID NO: 21). The two ribozymes differ by one nucleotide. See FIG. 3B; compare SEQ ID NO: 20 with SEQ ID NO: 21; also compare SEQ ID NO: 16 with SEQ ID NO: 17.

For cloning LTRhsp-MzgRNA-mpolyA-Cas9pA, two fragments were prepared by PCR then digested and ligated. The first fragment, MzgRNA-mpolyA, was created in two steps. In the first step, a fragment with part of the Mz ribozyme, gRNA, and mpolyA was prepared using the 5' primer of SEQ ID NO: 8 and the 3' primer of SEQ ID NO: 6. In the next step, PCR with the 5' primer of SEQ ID NO: 9 (containing EcoR1 site GAATTC) and the 3' primer of SEQ ID NO: 6 created the entire ribozyme with gRNA, the minimal polyA, and a 5' EcoR1 site (i.e., MzgRNA-mpolyA). The second fragment comprised the HIV LTR-minimal *Drosophila* hsp70 fusion promoter with a 3' EcoR1 site. It was amplified using the primers of SEQ ID NO: 1 and SEQ ID NO: 7 (containing a 3' EcoR1 site). The two fragments were digested with EcoR1 and ligated. Following ligation, the entire LTRhsp-MzgRNA-mpolyA was PCR-amplified using the primers of SEQ ID NO: 1 and SEQ ID NO: 6 (containing XbaI site TCTAGA). The PCR product was then digested with KpnI and XbaI and then ligated in similarly digested LTRhsp-gRNA-mpolyA-Cas9pA. This substituted LTRhsp-gRNA-mpolyA with LTRhsp-MzgRNA-mpolyA to generate the "Mz" ribozyme-embedded fragment, identified herein as LTRhsp-MzgRNA-mpolyA-Cas9pA (SEQ ID NO: 19).

Similarly, for cloning LTRhsp-Mz$_{wk}$gRNA-mpolyA-Cas9pA, two fragments were prepared by PCR then digested and ligated. The first fragment, Mz$_{wk}$gRNA-mpolyA, was created in two steps. First, a fragment with part of the "weak" ribozyme, gRNA, and mpolyA was created using the 5' primer of SEQ ID NO: 10 and the 3' primer of SEQ ID NO: 6. In the next step, the entire weak ribozyme with the minimal polyA was created using the 5' primer of SEQ ID NO: 9 and the 3' primer of SEQ ID NO: 6. (SEQ ID NO: 9 is a common primer that amplifies both the partial forms of Mz and Mz$_{wk}$ ribozymes to generate the full forms.) The second fragment was the same HIV LTR-minimal Drosophila hsp70 fusion promoter with a 3' EcoR1 site that was used to create LTRhsp-MzgRNA-mpolyA-Cas9pA. The two fragments were digested with EcoR1 and ligated. Following ligation, the entire LTRhsp-Mz$_{wk}$gRNA-mpolyA was amplified using the primers of SEQ ID NO: 1 and SEQ ID NO: 6. The PCR product was then digested with KpnI and XbaI and then ligated in similarly digested LTRhsp-gRNA-mpolyA-Cas9pA. This substituted LTRhsp-gRNA-mpolyA with LTRhsp-Mz$_{wk}$gRNA-mpolyA to generate the "Mz$_{wk}$" ribozyme-embedded fragment, identified herein as LTRhsp-Mz$_{wk}$gRNA-mpolyA-Cas9pA, which differs by one nucleotide from SEQ ID NO: 19.

All PCR amplifications in this Example were performed using the high-fidelity Vent$_R$® DNA Polymerase (New England Biolabs, #M0254S). The presence of ribozyme was confirmed by restriction digestion with KpnI and XbaI (FIG. 5).

Example 3: Confirmation of the Presence of Ribozyme by Restriction Digestion

In order to confirm the presence of ribozymes in LTRhsp-MzgRNA-mpolyA-Cas9pA and LTRhsp-Mz$_{wk}$gRNA-mpolyA-Cas9pA, the ligation mix was transformed in E. coli DH5-Alpha strain. The transformation was plated, and following overnight incubation, colonies were individually selected then grown in Luria broth with Ampicillin (100 µg/ml). Plasmid DNA was isolated and analyzed for the presence of the above expression inserts by restriction digestion with KpnI and XbaI and analyzed with electrophoresis. FIG. 5 shows the results of gel electrophoresis of the digested plasmids. Lanes 1 through 4 show screening of LTRhsp-MzgRNA-mpolyA-Cas9pA clones by restriction digestion with KpnI and XbaI. Lane 5 is 1 kb DNA ladder. Lanes 6-10 are screening of LTRhsp-Mz$_{wk}$gRNA-mpolyA-Cas9pA again after restriction digestion with KpnI and XbaI. Clones 1 and 4 showed the correct sized bands (766 bp) for LTRhsp-MzgRNA-mpolyA-Cas9pA (indicated with an arrow in FIG. 5), and Clone 1 (from lane 1) was selected for further experiments. Likewise, all clones screened for LTRhsp-Mz$_{wk}$gRNA-mpolyA-Cas9pA showed the correct sized band (indicated with the same arrow in FIG. 5). Clone 5 (from lane 10) was selected for further experiments.

Example 4: Conditional Expression of Cas9 Driven by HIV LTR-Minimal Drosophila Hsp70 Fusion Promoter and the Effects of NF-κβ or SP1 Deletions A study was performed to determine whether LTRhsp-gRNA-mpolyA-Cas9pA can conditionally drive expression of Cas9, in the presence of HIV-1 TAT protein. The HIV-1 LTR promoter of LTRhsp-gRNA-mpolyA-Cas9pA contains two transcription factor sites, NF-κβ and SP1, which were suspected to cause TAT-independent transcription. If it did, TAT-independent transcription could result in "leaky" or a basal level expression of Cas9. Therefore, the study included NF-κβ and SP1 deletion mutants of LTRhsp-gRNA-mpolyA-Cas9pA to determine the effects of deletion of the NF-κβ and SP1 sites on Cas9 expression. As used herein, LTR(ΔNF-κβ)-gRNA-mpolyA-Cas9pA and LTR(ΔSP1)-gRNAmpolyA-Cas9pA indicate the NF-κβ deletion mutant and the SP1 deletion mutant respectively.

HIV-infected HeLa-CD4 cells were transfected with LTRhsp-gRNA-mpolyA-Cas9pA, LTR(ΔNF-κβ)-gRNA-mpolyA-Cas9pA, or LTR(ΔSP1)-gRNAmpolyA-Cas9pA. Uninfected Hela-CD4 cells were identically transfected for comparison. Lentiviral vector backbone pHIV-7-GFP was again used as a control. 72-hours post-transfection, total protein was isolated and analyzed for Cas9 expression by western blot analyses, normalized to α-tubulin.

As shown in FIG. 2B, the LTRhsp-gRNA-mpolyA-Cas9pA construct according to the present invention expressed Cas9 in HIV-infected HeLa-CD4 cells in about a hundredfold increase after 72 hours post transfection. In contrast, virtually no expression was observed in the counterpart, uninfected HeLa-CD4 cells. The results demonstrated that LTRhsp-gRNA-mpolyA-Cas9pA is HIV-inducible. On the other hand, no expression of Cas9 was observed in either the HIV-infected or uninfected HeLa-CD4 cells transfected with LTR(ΔNF-κβ)-gRNA-mpolyA-Cas9pA. This suggested that NF-κβ sites are essential for the transcription of Cas9 from the HIV LTR-minimal Drosophila hsp70 fusion promoter. As for the cells transfected with the SPI deletion mutant, LTR(ΔSP1)-gRNA-mpolyA-Cas9pA, an appreciable level of Cas9 expression was observed in uninfected HeLa-CD4 cells, and a high Cas9 expression level was observed in the HIV-infected cells. This suggested that deletion of SP1 enhanced the "leakiness" of Cas9 expression.

Example 5: Demonstration of Conditional Cyclin T1 Knockdown Only in HIV-Infected Cells A study was conducted to determine whether HIV-inducible gRNA and Cas9 expression from LTRhsp-gRNAmpolyA-Cas9pA results in a conditional Cyclin T1 knockdown only in HIV-infected cells. HIV-infected and uninfected HeLa-CD4 cells were transfected with LTRhsp-gRNA-mpolyA-Cas9pA. Separately, HIV-infected and uninfected HeLa-CD4 cells were transfected with pLentiCRISPR-gRNA-2 for comparison, as this construct constitutively expresses gRNA-2. Lentiviral vector backbone pHIV-7-GFP was used as a control. 6-days post-transfection, experiments were terminated, and the total protein was analyzed for Cyclin T1 suppression by western blot analysis, normalized to α-tubulin. pLentiCRISPR-gRNA-2 suppressed Cyclin T1 protein levels in both HIV-infected (FIG.

2C) and uninfected (FIG. 2D) HeLa-CD4 cells, whereas LTRhsp-gRNA-mpolyA-Cas9pA of the present invention exhibited Cyclin T1 suppression only in HIV-infected HeLa-CD4 cells (FIG. 2C). No suppression of Cyclin T1 was observed by LTRhsp-gRNA-mpolyA-Cas9pA in uninfected HeLa-CD4 cells (FIG. 2D). The results demonstrated that the expression of LTRhsp-gRNA-mpolyA-Cas9pA is selectively inducible in HIV-infected HeLa-CD4 cells.

Example 6: Demonstration of Sustained HIV Suppression with LTRhsp-gRNAmpolyA-Cas9pA A study was conducted to observe the extent of suppression by LTRhsp-gRNA-Cas9pA of the present invention. HIV-infected HeLa-CD4 cells were transfected with LTRhsp-gRNA-mpolyA-Cas9pA. On day 6 post-transfection, cells were washed four times to remove any residual HIV p24 and resuspended in fresh DMEM with 10% FBS. The HIV p24 levels in the culture supernatant were assessed by HIV p24 ELISA as an indicator of HIV infection and replication, and Lipofectamine 2000 was used as a control. As shown in FIG. 2E, there was an approximately 75% suppression of HIV p24 mediated by the LTRhsp-gRNA-mpolyA-Cas9pA. However, the suppression efficacy was lower than that observed with the constitutive pLentiCRISPR-gRNA-2 for the same point (Example 1, FIG. 1B).

Example 7: Demonstration of Improvement of HIV Suppression with Embedded Ribozyme A study was conducted using two ribozyme-embedded variants—LTRhsp-MzgRNA-mpolyA-Cas9pA and LTRhsp-Mz$_{wk}$gRNA-mpolyA-Cas9pA—for their ability to suppress HIV replication in HIV-infected Hela-CD4 cells. LTRhsp-gRNAmpolyA-Cas9pA was also tested for comparison. To mimic a more physiological setting, only the transfection medium was replaced with fresh DMEM with 10% vol/vol FBS. At each time point of days 3, 6, 9, and 12 post-transfection, culture supernatants were collected and analyzed for HIV p24 levels as an indicator of HIV infection and replication. Transfection with the lentiviral backbone pHIV-7-GFP was used as a control and to monitor transfection.

Both LTRhsp-MzgRNA-mpolyA-Cas9pA and LTRhsp-Mz$_{wk}$gRNA-mpolyA-Cas9pA exhibited improved HIV suppression than the parent clone LTRhsp-gRNA-mpolyA-Cas9pA over 12 days post-transfection (Table 1 and corresponding FIG. 3C). Experiments were terminated after 12 days post-transfection, and cell viability and live cell count were determined. Table 2 and corresponding FIG. 3D show that all three HIV-inducible CRISPR system constructs do not adversely affect cell viability or the number of live cells as compared to the control. The overall results demonstrate that embedded ribozymes in LTRhsp-MzgRNA-mpolyA-Cas9pA and LTRhsp-Mz$_{wk}$gRNA-mpolyA-Cas9pA improve the HIV suppression efficacy while retaining cell viability.

TABLE 1

HIV p24 Levels at Each Time Point (pgs/ml)

| | pHIV-7-GFP | | LTRhsp-gRNA-mpolyA-Cas9pA | | LTRhsp-MzgRNA-mpolyA-Cas9pA | | LTRhsp-Mz$_{wk}$gRNA-mpolyA-Cas9pA | |
|---|---|---|---|---|---|---|---|---|
| | Mean | SEM | Mean | SEM | Mean | SEM | Mean | SEM |
| Day 3 | 6406667 | 500716.2 | 5248334 | 742919.4 | 8113334 | 2209461 | 7215000 | 830940.8 |
| Day 6 | 9678333 | 760931.4 | 7160000 | 897628.8 | 2540000 | 592842.8 | 3541667 | 587987.4 |
| Day 9 | 62608330 | 5370531 | 25706670 | 2427953 | 16861670 | 6037173 | 16830000 | 6211873 |
| Day 12 | 83586660 | 6088700 | 28073330 | 6906480 | 13180000 | 3124572 | 18911670 | 960809.1 |

SEM = Standard error of the mean
N = 3

TABLE 2

Live Cells and Percent Cell Viability After 12 Days Post-Transfection

| | Live Cells | | % Viability | |
|---|---|---|---|---|
| | Mean | SEM | Mean | SEM |
| pHIV-7-GFP | 1390000 | 129807.6 | 92.75243 | 1.951525 |
| LTRhsp-gRNA-mpolyA-Cas9pA | 1365333 | 284398.8 | 93.80446 | 2.269045 |
| LTRhsp-MzgRNA-mpolyA-Cas9pA | 1383333 | 96263.52 | 97.20004 | 0.9065809 |
| LTRhsp-Mz$_{wk}$gRNA-mpolyA-Cas9pA | 1416667 | 246001.4 | 95.90449 | 0.989395 |

SEM = Standard error of the mean
N = 3

Example 8: System Efficacy in CEM T-Cells (with or without Ribozyme)

To investigate the potential of the HIV-inducible CRISPR systems of the present invention in a more physiologically relevant host, CEM T-cells were infected with HIV IIIB strain. The infection was allowed to proceed for 12 days. HIV p24 levels were monitored to follow the progress of infection. Following 12 days of infection, infected cultures were divided into different experimental sets and then electroporated with either the original LTRhsp-gRNA-mpolyA-Cas9pA, or the minizyme-embedded constructs LTRhsp-MzgRNA-mpolyA-Cas9pA or LTRhsp-Mz$_{wk}$gRNA-mpolyA-Cas9pA, using the Neon electroporation kit. Lentiviral vector pHIV-7-GFP was electroporated as a control and to follow electroporation efficiency. Approximately 90% electroporation efficiency was observed using the Neon electroporation kit. The infection of CEM T-cells was allowed to proceed for additional 12 days, during which culture supernatants were collected for p24 analyses every 3 days.

All three HIV-inducible CRISPR systems according to the present invention demonstrated HIV suppression that persisted up to 12 days post-electroporation (see Table 3 and corresponding FIG. 4A). Specifically, the parent LTRhsp-gRNA-mpolyA-Cas9pA demonstrated maximum suppression by day 6 followed by a progressive increase in p24 levels on days 9 and 12 with 53% HIV suppression observed on Day 12. Both minizyme-embedded constructs demonstrated better efficacy and more sustained HIV suppression compared to the parent LTRhsp-gRNA-mpolyA-Cas9pA without an embedded ribozyme. While there was an observable trend of LTRhsp-Mz$_{wk}$gRNA-mpolyA-Cas9pA (having the "weak" minizyme using the non-canonical GUG site) demonstrating better HIV suppression than LTRhsp-MzgRNA-mpolyA-Cas9pA (having the minizyme using the canonical GUC cleavage site), the data was not statistically significant. Cell viability and count were determined on day 12 using trypan blue staining. The results in Table 4 (corresponding FIG. 4B) show that none of the HIV-inducible CRISPR systems according to the present invention demonstrated a significant decrease in cell viability or the number of live cells compared to the control.

TABLE 3

HIV p24 Levels at Each Time Point (pgs/ml)

| | pHIV-7-GFP | | LTRhsp-gRNA-mpolyA-Cas9pA | | LTRhsp-MzgRNA-mpolyA-Cas9pA | | LTRhsp-Mz$_{wk}$gRNA-mpolyA-Cas9pA | |
|---|---|---|---|---|---|---|---|---|
| | Mean | SEM | Mean | SEM | Mean | SEM | Mean | SEM |
| Day 3 | 4044125 | 975217.5 | 781375 | 181996.9 | 538125 | 199332 | 572625 | 80673 |
| Day 6 | 3449875 | 838524 | 250625 | 12060.9 | 197075 | 64010.47 | 250625 | 49846.64 |
| Day 9 | 3475125 | 387728.4 | 773925 | 257999 | 181763 | 45209.73 | 248513 | 44988.03 |
| Day 12 | 4166025 | 379191.8 | 1965475 | 452472.1 | 1094488 | 102063 | 763350 | 430085 |

SEM = Standard error of the mean
N = 4

TABLE 4

Live Cells and Percent Cell Viability After 12 Days Post-Transfection

| | Live Cells | | % Viability | |
|---|---|---|---|---|
| | Mean | SEM | Mean | SEM |
| pHIV-7-GFP | 4690000 | 98319.21 | 66.0602 | 3.109915 |
| LTRhsp-gRNA-mpolyA-Cas9pA | 4522500 | 802542.8 | 72.50906 | 3.996425 |
| LTRhsp-MzgRNA-mpolyA-Cas9pA | 3967500 | 359641 | 74.94627 | 3.032196 |
| LTRhsp-Mz$_{wk}$gRNA-mpolyA-Cas9pA | 4595000 | 623137.3 | 77.57472 | 7.964862 |

SEM = Standard error of the mean
N = 4

All patents, patent applications, provisional applications, and publications referred to or cited herein are incorporated by reference in their entirety, including all figures and tables, to the extent they are not inconsistent with the explicit teachings of this specification.

The invention claimed is:

1. An inducible Clustered, Regularly Interspaced, Short Palindromic Repeats (CRISPR) system comprising, in the 5' to 3' direction:
   an inducible fusion promoter comprising a minimal Drosophila hsp70 promoter that is operatively associated with an inducible element;
   a nucleotide sequence encoding a modified ribozyme having lower cleavage efficiency than before the modification;
   a nucleotide sequence encoding a guide RNA (gRNA), said nucleotide sequence encoding a modified ribozyme being immediately upstream of said nucleotide sequence encoding a gRNA;
   a minimal polyadenylation signal sequence; and
   a nucleotide sequence encoding a CRISPR associated protein (Cas),
said inducible fusion promoter being inducible by an inducer to drive expression of said gRNA and said Cas,
said nucleotide sequence encoding a modified ribozyme being the only ribozyme-encoding nucleotide sequence being operatively associated with said nucleotide sequence encoding a gRNA, said modified ribozyme comprising the nucleotide sequence of SEQ ID NO: 16 or SEQ ID NO: 17, and said system being capable of expressing said modified ribozyme and said gRNA, and, when expressed, said modified ribozyme being capable of removing a 5' cap of the gRNA.

2. The inducible CRISPR system of claim 1, said modified ribozyme being a cis-cleaving ribozyme.

3. The inducible CRISPR system of claim 1, said modified ribozyme being a modified hammerhead ribozyme.

4. The inducible CRISPR system of claim 1, said Cas being a Cas9.

5. The inducible CRISPR system of claim 1, further comprising a eukaryotic translation initiation site upstream of said nucleotide sequence encoding a Cas and downstream of said minimal polyadenylation signal sequence.

6. The inducible CRISPR system of claim 1, said inducible element being human immunodeficiency virus type 1 long terminal repeat (HIV-1 LTR).

7. The inducible CRISPR system of claim 6, said gRNA targeting Cyclin T1.

8. An isolated cell comprising the inducible CRISPR system of claim 1.

9. The isolated cell of claim 8, further being infected with a virus.

10. The isolated cell of claim 9, said virus being HIV.

11. A method of altering expression of at least one gene product in a cell:
    introducing into the cell an inducible CRISPR system of claim 1 in an amount sufficient to alter expression of said at least one gene product,
    said inducible CRISPR system being induced by an inducer, and
    expression of said at least one gene product being altered in the cell.

12. The method according to claim 11, said expression being reduced.

13. The method according to claim 11, said cell being infected with HIV.

14. A method of suppressing viral replication in a cell infected with a virus:
    introducing into said cell an inducible CRISPR system of claim 1 in an amount sufficient to suppress viral replication,
    said inducible CRISPR system being induced by an inducer, and
    replication of said virus being suppressed in the cell.

15. The method according to claim 14, said virus being HIV.

16. The inducible CRISPR system of claim 1, said inducible element comprising the sequence of SEQ ID NO: 11.

17. The inducible CRISPR system of claim 1, said nucleotide sequence encoding said gRNA comprising the sequence of SEQ ID NO: 13, 14 or 15.

18. The inducible CRISPR system of claim 1, the 5' cap being a 5'-methyl guanosine cap.

19. The inducible CRISPR system of claim 1, the minimal Drosophila hsp70 promoter being SEQ ID NO: 12.

* * * * *